United States Patent
Harris, Sr. et al.

(10) Patent No.: US 10,423,759 B1
(45) Date of Patent: Sep. 24, 2019

(54) SYSTEMS AND METHODS FOR IDENTIFYING PRIOR AUTHORIZATION ASSISTANCE REQUESTS IN HEALTHCARE TRANSACTIONS

(71) Applicant: MCKESSON CORPORATION, San Francisco, CA (US)

(72) Inventors: Patrick I. Harris, Sr., Atlanta, GA (US); Roger G. Pinsonneault, Alpharetta, GA (US)

(73) Assignee: MCKESSON CORPORATION, San Francisco, CA (US)

(*) Notice: Subject to any disclaimer, the term of this patent is extended or adjusted under 35 U.S.C. 154(b) by 1096 days.

(21) Appl. No.: 14/598,968

(22) Filed: Jan. 16, 2015

(51) Int. Cl.
G06F 19/00 (2018.01)
G16H 20/00 (2018.01)

(52) U.S. Cl.
CPC .......... *G06F 19/328* (2013.01); *G16H 20/00* (2018.01)

(58) Field of Classification Search
CPC ........ G06Q 50/22; G06Q 50/24; G06Q 40/08; G06Q 30/04; G06F 19/328; G06F 19/322
See application file for complete search history.

(56) References Cited

U.S. PATENT DOCUMENTS

| | | | |
|---|---|---|---|
| 3,732,546 A | 5/1973 | Ronkin et al. | |
| 3,900,834 A | 8/1975 | Casey et al. | |
| 4,276,597 A | 6/1981 | Dissly et al. | |
| 4,674,041 A | 6/1987 | Lemon et al. | |
| 4,723,212 A | 2/1988 | Mindrum et al. | |
| 4,910,672 A | 3/1990 | Off et al. | |
| 5,007,641 A | 4/1991 | Seidman | |

(Continued)

FOREIGN PATENT DOCUMENTS

| CA | 2482370 | 3/2006 |
|---|---|---|
| WO | 1995003569 | 2/1995 |

(Continued)

OTHER PUBLICATIONS

Sampson, R.J., Taking Control of Health Care Costs, Best's Review—Life Health Insurance Edition, Nov. 1983, vol. 84, Issue 7, USA; Abstract only.

(Continued)

*Primary Examiner* — Jonathan Durant
(74) *Attorney, Agent, or Firm* — Alston & Bird LLP

(57) ABSTRACT

An adjudicated response to a healthcare transaction for a product or service for a patient is received and includes a transaction submission time, and transaction comparison data. The transaction comparison data can be compared to a multitude of transaction records of previously processed healthcare transactions to identify a match. The transaction submission time for each of the received healthcare transaction and stored healthcare transaction can be received and compared to one another to determine a submission time difference between the submission time for the healthcare transaction and the stored healthcare transaction. The submission time difference can be compared to a time limit threshold to determine if the difference satisfies the time limit threshold. Based on the determination that the submission time difference satisfies the threshold, the received healthcare transaction can be determined to be a request for a service, such as prior authorization assistance.

20 Claims, 9 Drawing Sheets

(56) References Cited

U.S. PATENT DOCUMENTS

| | | |
|---|---|---|
| 5,080,364 A | 1/1992 | Seidman |
| 5,173,851 A | 12/1992 | Off et al. |
| 5,201,010 A | 4/1993 | Deaton et al. |
| 5,237,620 A | 8/1993 | Deaton et al. |
| 5,305,196 A | 4/1994 | Deaton et al. |
| 5,327,508 A | 7/1994 | Deaton et al. |
| 5,388,165 A | 2/1995 | Deaton et al. |
| 5,430,644 A | 7/1995 | Deaton et al. |
| 5,448,471 A | 9/1995 | Deaton et al. |
| 5,588,649 A | 12/1996 | Blumberg et al. |
| 5,592,560 A | 1/1997 | Deaton et al. |
| 5,612,868 A | 3/1997 | Off et al. |
| 5,621,812 A | 4/1997 | Deaton et al. |
| 5,628,530 A | 5/1997 | Thornton |
| 5,638,457 A | 6/1997 | Deaton et al. |
| 5,642,485 A | 6/1997 | Deaton et al. |
| 5,644,723 A | 7/1997 | Deaton et al. |
| 5,649,114 A | 7/1997 | Deaton et al. |
| 5,659,469 A | 8/1997 | Deaton et al. |
| 5,675,662 A | 10/1997 | Deaton et al. |
| 5,687,322 A | 11/1997 | Deaton et al. |
| 5,832,457 A | 11/1998 | O'Brien |
| 5,845,255 A | 12/1998 | Mayaud |
| 5,857,175 A | 1/1999 | Day et al. |
| 5,892,827 A | 4/1999 | Beach et al. |
| 5,915,007 A | 6/1999 | Klapka |
| 5,926,795 A | 7/1999 | Williams |
| 5,970,469 A | 10/1999 | Scroggie et al. |
| 5,974,399 A | 10/1999 | Giuliani et al. |
| 6,012,035 A | 1/2000 | Freeman, Jr. et al. |
| 6,014,634 A | 1/2000 | Scroggie et al. |
| 6,021,392 A | 2/2000 | Lester et al. |
| 6,026,370 A | 2/2000 | Jermyn |
| 6,041,309 A | 3/2000 | Laor |
| 6,055,573 A | 4/2000 | Gardenswartz et al. |
| 6,067,069 A | 5/2000 | Krause |
| 6,067,524 A | 5/2000 | Byerly et al. |
| 6,088,677 A | 7/2000 | Spurgeon |
| 6,185,541 B1 | 2/2001 | Scroggie et al. |
| 6,195,612 B1 | 2/2001 | Pack-Harris |
| 6,202,923 B1 | 3/2001 | Boyer et al. |
| 6,205,455 B1 | 3/2001 | Umen |
| 6,240,394 B1 | 5/2001 | Uecker |
| 6,260,758 B1 | 7/2001 | Blumberg |
| 6,278,979 B1 | 8/2001 | Williams |
| 6,282,516 B1 | 8/2001 | Giuliani |
| 6,298,330 B1 | 10/2001 | Gardenswartz et al. |
| 6,304,849 B1 | 10/2001 | Uecker et al. |
| 6,307,958 B1 | 10/2001 | Deaton et al. |
| 6,321,210 B1 | 11/2001 | O'Brien et al. |
| 6,334,108 B1 | 12/2001 | Deaton et al. |
| 6,343,271 B1 | 1/2002 | Peterson |
| 6,377,935 B1 | 4/2002 | Deaton et al. |
| 6,424,949 B1 | 7/2002 | Deaton et al. |
| 6,484,146 B2 | 11/2002 | Day et al. |
| 6,584,448 B1 | 6/2003 | Laor |
| 6,684,195 B1 | 1/2004 | Deaton et al. |
| 6,757,898 B1 | 6/2004 | Ilsen et al. |
| 6,769,228 B1 | 8/2004 | Mahar |
| 6,795,809 B2 | 9/2004 | O'Brien et al. |
| 6,885,994 B1 | 4/2005 | Scroggie et al. |
| 7,024,374 B1 | 4/2006 | Day et al. |
| 7,058,584 B2 | 6/2006 | Kosinski et al. |
| 7,058,591 B2 | 6/2006 | Giuliani et al. |
| 7,155,397 B2 | 12/2006 | Alexander et al. |
| 7,225,052 B2 | 5/2007 | Foote et al. |
| 7,227,842 B1* | 6/2007 | Ji .................... H04L 45/00 370/235 |
| 7,228,285 B2 | 6/2007 | Hull et al. |
| 7,233,913 B2 | 6/2007 | Scroggie et al. |
| 7,309,001 B2 | 12/2007 | Banfield et al. |
| 7,415,426 B2 | 8/2008 | Williams et al. |
| 7,426,480 B2 | 9/2008 | Granger et al. |
| 7,685,006 B2 | 3/2010 | Rahn et al. |
| 7,711,660 B1 | 5/2010 | Gentile et al. |
| 7,716,065 B1 | 5/2010 | Maxwell |
| 7,926,709 B1 | 4/2011 | Dooley et al. |
| 8,392,214 B1* | 3/2013 | Pinsonneault ......... G06Q 50/22 235/378 |
| 8,438,047 B2 | 5/2013 | Curtin et al. |
| 8,548,824 B1 | 10/2013 | daCosta |
| 8,639,523 B1 | 1/2014 | Pinsonneault |
| 2001/0027403 A1 | 10/2001 | Peterson et al. |
| 2002/0002495 A1 | 1/2002 | Ullman |
| 2002/0019754 A1 | 2/2002 | Peterson et al. |
| 2002/0087583 A1 | 7/2002 | Morgan et al. |
| 2002/0111832 A1 | 8/2002 | Judge |
| 2002/0198831 A1 | 12/2002 | Patricelli et al. |
| 2003/0009367 A1 | 1/2003 | Morrison |
| 2003/0050799 A1 | 3/2003 | Jay et al. |
| 2003/0074218 A1 | 4/2003 | Liff et al. |
| 2003/0074225 A1 | 4/2003 | Borsand et al. |
| 2003/0125986 A1 | 7/2003 | Collosi |
| 2003/0149625 A1 | 8/2003 | Leonardi et al. |
| 2003/0154163 A1 | 8/2003 | Phillips et al. |
| 2003/0229540 A1 | 12/2003 | Algiene |
| 2004/0006490 A1 | 1/2004 | Gingrich |
| 2004/0039599 A1 | 2/2004 | Fralic |
| 2004/0049422 A1 | 3/2004 | Mortimer |
| 2004/0054657 A1 | 3/2004 | Takeyama |
| 2004/0054685 A1 | 3/2004 | Rahn et al. |
| 2004/0073457 A1 | 4/2004 | Kalies et al. |
| 2004/0078234 A1 | 4/2004 | Tallal, Jr. et al. |
| 2004/0078247 A1 | 4/2004 | Rowe et al. |
| 2004/0078724 A1 | 4/2004 | Keller et al. |
| 2004/0107117 A1 | 6/2004 | Denny |
| 2004/0111277 A1 | 6/2004 | Pearson et al. |
| 2004/0117323 A1 | 6/2004 | Mindala |
| 2004/0133452 A1 | 7/2004 | Denny |
| 2004/0148198 A1 | 7/2004 | Kalies |
| 2004/0153336 A1 | 8/2004 | Virdee et al. |
| 2004/0225528 A1 | 11/2004 | Brock |
| 2004/0249745 A1 | 12/2004 | Baaren |
| 2005/0015280 A1 | 1/2005 | Gabel et al. |
| 2005/0033610 A1 | 2/2005 | Cunningham |
| 2005/0060201 A1 | 3/2005 | Connely, III et al. |
| 2005/0071193 A1 | 3/2005 | Kalies |
| 2005/0086081 A1 | 4/2005 | Brock-Fisher |
| 2005/0090425 A1 | 4/2005 | Reardan et al. |
| 2005/0102169 A1 | 5/2005 | Wilson |
| 2005/0108067 A1* | 5/2005 | Chapman ............... G06Q 10/10 705/4 |
| 2005/0154627 A1 | 7/2005 | Zuzek et al. |
| 2005/0171815 A1 | 8/2005 | Vanderveen |
| 2005/0187793 A1 | 8/2005 | Myles |
| 2005/0197862 A1 | 9/2005 | Paterson et al. |
| 2005/0222874 A1 | 10/2005 | Reardan et al. |
| 2005/0228766 A1 | 10/2005 | Roberts et al. |
| 2005/0240473 A1 | 10/2005 | Ayers, Jr. et al. |
| 2005/0288972 A1 | 12/2005 | Marvin et al. |
| 2006/0015518 A1 | 1/2006 | Eletreby et al. |
| 2006/0020514 A1 | 1/2006 | Yered |
| 2006/0026041 A1 | 2/2006 | Ullman |
| 2006/0116907 A1 | 6/2006 | Rhodes et al. |
| 2006/0129433 A1 | 6/2006 | Koneru |
| 2006/0149587 A1 | 7/2006 | Hill, Sr. et al. |
| 2006/0149784 A1 | 7/2006 | Tholl et al. |
| 2006/0161453 A1 | 7/2006 | Kost et al. |
| 2006/0184391 A1 | 8/2006 | Barre et al. |
| 2006/0224415 A1 | 10/2006 | Hudson et al. |
| 2006/0229915 A1 | 10/2006 | Kosinski et al. |
| 2006/0259363 A1 | 11/2006 | Jhetam et al. |
| 2006/0271398 A1 | 11/2006 | Belcastro |
| 2006/0287886 A1 | 12/2006 | Kitazawa |
| 2007/0005402 A1 | 1/2007 | Kennedy et al. |
| 2007/0050209 A1 | 3/2007 | Yered |
| 2007/0088576 A1 | 4/2007 | de Beus et al. |
| 2007/0124177 A1 | 5/2007 | Engleson et al. |
| 2007/0136100 A1 | 6/2007 | Daugherty et al. |
| 2007/0162303 A1 | 7/2007 | Wiley et al. |
| 2007/0179957 A1 | 8/2007 | Gibson et al. |
| 2007/0233525 A1 | 10/2007 | Boyle |
| 2007/0233526 A1 | 10/2007 | Hoffman et al. |
| 2007/0239493 A1 | 10/2007 | Sweetland et al. |

(56) References Cited

U.S. PATENT DOCUMENTS

| | | | |
|---|---|---|---|
| 2008/0103836 | A1 | 5/2008 | Park et al. |
| 2008/0288281 | A1 | 11/2008 | Shell |
| 2009/0024412 | A1 | 1/2009 | Medvitz et al. |
| 2009/0055225 | A1 | 2/2009 | Russell |
| 2009/0144088 | A1 | 6/2009 | Zubiller et al. |
| 2009/0164376 | A1 | 6/2009 | Guthrie |
| 2009/0198518 | A1 | 8/2009 | McKenzie et al. |
| 2010/0217973 | A1 | 8/2010 | Kress et al. |
| 2010/0235197 | A1* | 9/2010 | Dang ............... G06F 19/328 705/3 |
| 2010/0241445 | A1 | 9/2010 | Rago et al. |
| 2010/0256985 | A1* | 10/2010 | Nix .................. G06Q 10/067 705/2 |
| 2010/0268550 | A1 | 10/2010 | Abuzeni et al. |
| 2011/0029321 | A1* | 2/2011 | Rourke ........... G06F 17/30896 705/2 |
| 2011/0126273 | A1 | 5/2011 | Bhatia et al. |
| 2011/0137673 | A1 | 6/2011 | Burk et al. |
| 2011/0178812 | A1 | 7/2011 | Lindsay |
| 2011/0257992 | A1 | 10/2011 | Scantland et al. |
| 2011/0282690 | A1 | 11/2011 | Patel |
| 2012/0109839 | A1 | 5/2012 | Anderson et al. |
| 2012/0150561 | A1 | 6/2012 | Carroll |
| 2012/0185270 | A1 | 7/2012 | Scantland et al. |
| 2013/0041676 | A1* | 2/2013 | Momita ............ G06Q 50/18 705/2 |
| 2014/0297298 | A1 | 10/2014 | Rago |

FOREIGN PATENT DOCUMENTS

| | | |
|---|---|---|
| WO | 2000039737 | 7/2000 |
| WO | 2007025295 | 3/2007 |

OTHER PUBLICATIONS

Anonymous, ACS to Demonstrate Electronic Health Record Solution Suite at MMIS 2007 Conference; EHR Tools Consolidate Data, Provide Useful Information at the Point of Care for Medicaid Providers, Payers, and Patients, PR Newswire, Aug. 13, 2007, New York, NY, USA.

Lamb, J., New Era of Electronic Medicine Management: E-Prescriptions, Britain's Traditionally Cautious National Health Service is Starting Trials for Online Prescription, with the Aim of Cutting Costs. Financial Times, London, Feb. 21, 2001, p. 6, London, United Kingdom.

Anonymous, Pharmacy Industry Leaders Launch Firm to Supply Real-Time Data. PR Newswire. Jul. 30, 2001, p. 1, New York, NY, USA.

Anonymous, Medic; On-line Goes In-House, Chain Store Age Executive, Jan. 1987, vol. 63, Issue 1, USA; Abstract only.

Anonymous, TechRx Announces Successful Beta Deployment of T-Rex. PR Newswire. May 13, 2002.

Google patents search dated Sep. 11, 2012.

Non-Final Office Action for U.S. Appl. No. 12/605,946 dated Dec. 9, 2011.

Final Office Action for U.S. Appl. No. 12/605,946 dated Mar. 21, 2012.

Non-Final Office Action for U.S. Appl. No. 13/071,567 dated Oct. 5, 2012.

Notice of Allowance for U.S. Appl. No. 12/957,106 dated Oct. 18, 2012.

Non-Final Office Action for U.S. Appl. No. 13/112,782 dated Dec. 27, 2012.

Final Office Action for U.S. Appl. No. 13/071,567 dated Mar. 21, 2013.

Final Office Action for U.S. Appl. No. 13/112,782 dated Jul. 5, 2013.

Non-Final Office Action for U.S. Appl. No. 12/982,371 dated Aug. 22, 2013.

Non-Final Office Action for U.S. Appl. No. 12/605,946 dated Nov. 6, 2013.

Final Office Action for U.S. Appl. No. 12/982,371 dated Feb. 11, 2014.

Non-Final Office Action for U.S. Appl. No. 13/406,113 dated Mar. 28, 2014.

Final Office Action for U.S. Appl. No. 12/605,946 dated Jun. 3, 2014.

Non-Final Office Action for U.S. Appl. No. 13/406,113 dated Oct. 9, 2014.

Non-Final Office Action for U.S. Appl. No. 13/112,782 dated Dec. 4, 2014.

Non-Final Office Action for U.S. Appl. No. 12/605,946 dated Jan. 2, 2015.

Non-final Office Action for U.S. Appl. No. 12/982,371 dated Mar. 23, 2015.

Non-final Office Action for U.S. Appl. No. 14/486,292 dated Apr. 6, 2015.

Final Office Action for U.S. Appl. No. 13/112,782 dated Apr. 9, 2015.

Final Office Action for U.S. Appl. No. 12/605,946 dated Jul. 15, 2015.

Final Office Action for U.S. Appl. No. 12/982,371 dated Sep. 22, 2015.

Non-final Office Action for U.S. Appl. No. 13/929,383 dated Oct. 1, 2015.

Non-final Office Action for U.S. Appl. No. 13/406,113 dated Dec. 18, 2015.

Non-final Office Action for U.S. Appl. No. 13/853,385 dated Oct. 26, 2015.

Non-final Office Action for U.S. Appl. No. 13/112,782 dated Oct. 23, 2015.

Final Office Action for U.S. Appl. No. 14/486,292 dated Oct. 8, 2015.

Final Office Action for U.S. Appl. No. 13/112,782 dated Sep. 2, 2016.

Letter Restarting Period for Reply for U.S. Appl. No. 13/853,385 dated Nov. 30, 2016.

Non-Final Office Action for U.S. Appl. No. 12/982,371 dated Jan. 5, 2017.

Non-Final Office Action for U.S. Appl. No. 14/486,292 dated Jan. 11, 2017.

Final Office Action for U.S. Appl. No. 13/406,113 dated Jul. 14, 2016.

Final Office Action for U.S. Appl. No. 13/929,383 dated Mar. 21, 2016.

Final Office Action for U.S. Appl. No. 13/853,385 dated May 20, 2016.

Non-Final Office Action for U.S. Appl. No. 13/071,567 dated Jan. 8, 2018.

Non-Final Office Action for U.S. Appl. No. 13/071,567 dated Jun. 23, 2017.

Non-Final Office Action for U.S. Appl. No. 13/853,385 dated Aug. 2, 2017.

Non-Final Office Action for U.S. Appl. No. 13/853,385 dated Feb. 9, 2018.

Non-Final Office Action for U.S. Appl. No. 13/853,385 dated Jun. 28, 2018.

Non-Final Office Action for U.S. Appl. No. 14/511,564 dated Aug. 30, 2018.

Non-Final Office Action for U.S. Appl. No. 14/511,564 dated May 24, 2017.

Non-Final Office Action for U.S. Appl. No. 14/511,564 dated Oct. 26, 2017.

Non-Final Office Action for U.S. Appl. No. 14/486,292 dated May 18, 2017.

Notice of Allowance for U.S. Appl. No. 12/957,106 dated Jan. 17, 2013.

U.S. Appl. No. 12/605,946, filed Oct. 26, 2009, In re: Pinsonneault entitled Systems and Methods for Billing Assistance Messaging.

U.S. Appl. No. 13/071,567, filed Mar. 25, 2011, In re: Pinsonneault entitled Systems and Methods for Including Prescriber Contact Information in Healthcare Transactions.

(56) References Cited

OTHER PUBLICATIONS

U.S. Appl. No. 14/486,292, filed Sep. 15, 2014, In re: Pinsonneault entitled Systems and Methods for Supporting Prior Authorization Inquiries.
U.S. Appl. No. 14/511,564, filed Oct. 10, 2014, In re: Pinsonneault entitled Systems and Methods for Billing Assistance Messaging.
Rx 30—The Pharmacy System. <http://web.archive.org/web/20100124142227/http://www.rx30.com/Products_Prescription_Processing.asp> Archived Jan. 24, 2010. Downloaded Apr. 2, 2015. 2 pages.
Non-Final Office Action for U.S. Appl. No. 13/406,113 dated Apr. 23, 2015.
Non-final Office Action for U.S. Appl. No. 13/929,383 dated Apr. 21, 2015.
U.S. Appl. No. 12/982,371, filed Dec. 30, 2010, In re: Pinsonneault entitled Systems and Methods for Supporting Prior Authorization Inquiries.
U.S. Appl. No. 13/112,782, filed May 20, 2011, In re: Pinsonneault entitled Systems and Methods for Providing Prior Authorization Assistance With Medication History Support.
U.S. Appl. No. 13/406,113, filed Feb. 27, 2012, In re: Pinsonneault entitled Systems and Methods for Capturing Prescriber Information.
U.S. Appl. No. 13/929,383, filed Jun. 27, 2013, In re: Burgett et al. entitled Systems and Methods for Validating Drug Substitution as Part of Prior Authorization Resubmission.
Office Action for U.S. Appl. No. 15/085,150 dated Aug. 8, 2019.

\* cited by examiner

SYSTEMS AND METHODS FOR IDENTIFYING PRIOR AUTHORIZATION ASSISTANCE REQUESTS IN HEALTHCARE TRANSACTIONS

TECHNICAL FIELD

Aspects of the disclosure relate generally to healthcare transactions, and more particularly, to systems and methods for comparing information in healthcare transactions and making inferences based on those comparisons with regard to whether assistance with prior authorization is being requested.

BACKGROUND

A healthcare provider, such as a pharmacy, pharmacist, doctor's office, urgent care center, physician, hospital, or the like provides numerous healthcare related services to patients. One of these services is to, at times, provide prescription medications, products, or services to a patient. Typically, a healthcare transaction, such as a predetermination of benefits transaction, healthcare claim transaction, prescription claim or billing request, healthcare order transaction, or e-prescription transaction (e.g., electronic prescription order transaction, e-script, or e-prescription), is generated by the healthcare provider and sent, either directly or indirectly, to a claims processor for adjudication. In some cases, the healthcare transaction is sent to a claims processor by way of a service provider or switch. The healthcare transaction typically includes information that identifies the patient, the medication, product, or service being requested, the healthcare provider (either the prescriber, pharmacy, or both), and the benefit plan, insurer, or government-funded payor for the patient.

In certain situations, in order for the patient to receive a requested medication, product, or service, the prescriber (e.g., physician, hospital, nurse or any person legally permitted to prescribe medications, products, and/or services) was supposed to first have received prior authorization from the benefit plan, insurer or government-funded payor. In situations where this has not occurred, the claims processor associated with the benefit plan, insurer, or government-funded payor may reject, as part of the adjudication, a healthcare transaction requesting prior authorization for the requested medication, product, or service. A prior authorization rejection or request is one where the pharmacy benefits manager, insurance company, or other benefits payor initially blocks a patient's coverage for a prescribed medication, product or service, and requires that the prescriber contact the payor to provide additional information to the payor. For example, the payor may want to make sure what is being prescribed is what the doctor intended to prescribe, that the medication is clinically appropriate, that a generic or other equivalent medication cannot be substituted for the prescribed medication, or that other alternative medications or therapies have been attempted or a reason given why they should not need to be attempted in this case.

When a prior authorization from the prescriber is needed, the claims processor will initially reject the healthcare transaction and inform the patient, by way of the service provider and the pharmacist and via a rejected adjudicated healthcare transaction response, that the rejection is due to a prior authorization requirement. The service provider may offer the patient and pharmacist a prior authorization assistance service to help satisfy the prior authorization requirement. However, in order to obtain this prior authorization assistance service, the pharmacist/pharmacy must reevaluate and make particular changes to the healthcare transaction which can be very disruptive to the workflow of and reduce the overall operating efficiency of the pharmacist and the pharmacy.

BRIEF DESCRIPTION OF THE DRAWINGS

Reference will now be made to the accompanying drawings, which are not necessarily drawn to scale, and wherein.

DETAILED DESCRIPTION OF EXEMPLARY EMBODIMENTS

Figure 1:
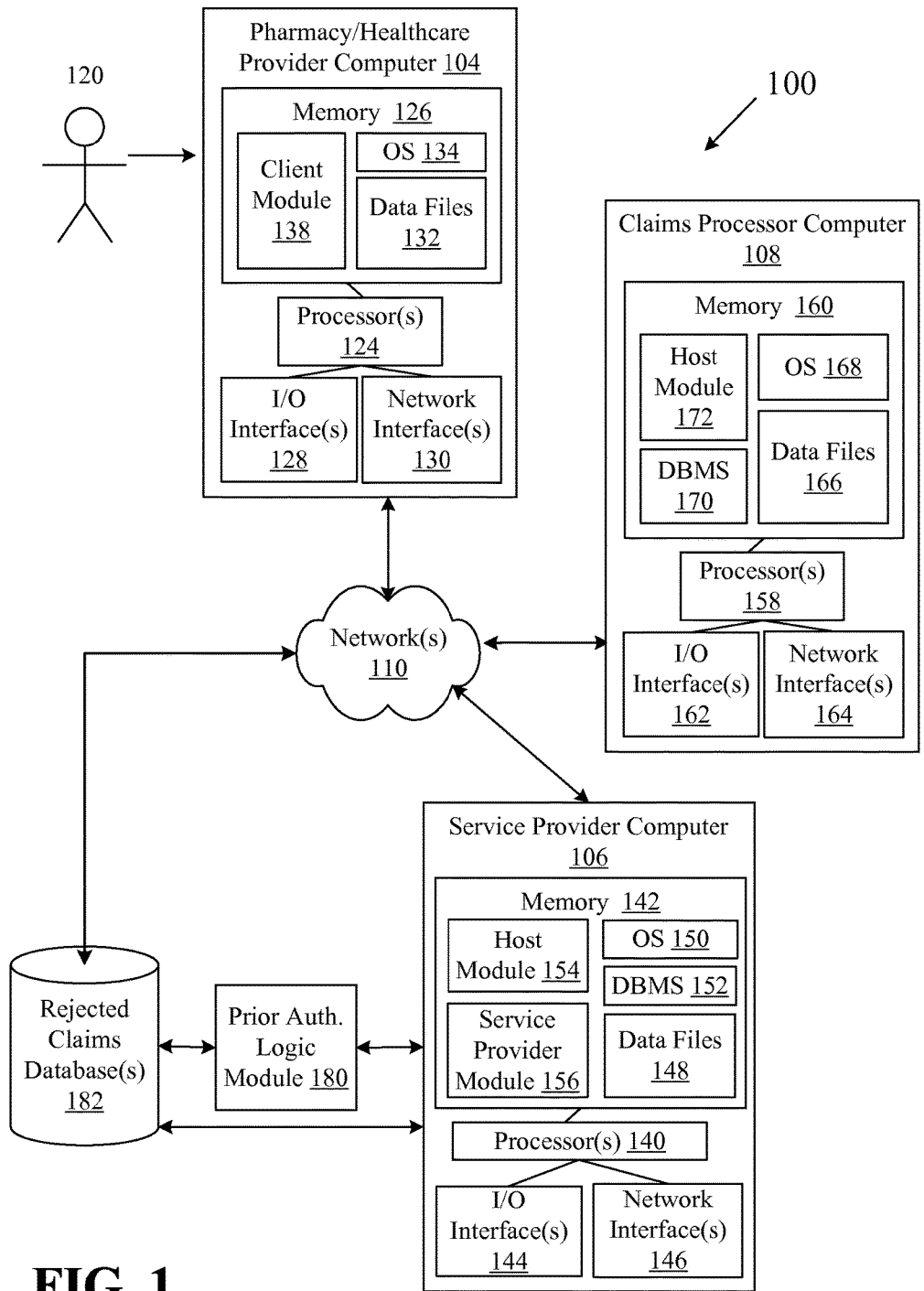
FIG. 1 illustrates an example overview of a system that facilitates the determination as to whether a request for prior authorization assistance is being made by a healthcare provider based on an evaluation of the data in the healthcare transaction as part of the processing of the healthcare transaction according to one exemplary embodiment.

Exemplary embodiments will now be described more fully hereinafter with reference to the accompanying drawings, in which example embodiments are shown. The concepts disclosed herein may, however, be embodied in many different forms and should not be construed as limited to the example embodiments set forth herein; rather, these embodiments are provided so that this disclosure will be thorough and complete, and will fully convey the scope of the concepts to those skilled in the art. Like numbers refer to like, but not necessarily the same or identical, elements throughout.

Example embodiments described herein include systems and methods that facilitate the determination as to whether a healthcare provider is making a request for prior authorization assistance based on an evaluation of the data in the healthcare transaction as part of or in-line with the processing of one or more types of healthcare transactions, such as a predetermination of benefits transaction, healthcare claim transaction, prescription claim or billing request, healthcare order transaction, or e-prescription transaction (e.g., electronic prescription order transaction, e-script, or e-prescription), in real-time or near real-time. For example, healthcare claim transactions may be received and evaluated by a service provider prior and/or subsequent to routing or otherwise communicating the healthcare claim transactions to various claims processors. The service provider may transmit the healthcare transaction to a claims processor for adjudication and receive back from the claims processor an adjudicated response. The service provider may determine if the transaction was approved and if not, the basis for rejecting the transaction. The service provider may further determine if the healthcare claim transaction was rejected for lack of prior authorization. If rejected for lack of prior authorization, the service provider may store the transaction, or the data therein, for subsequent analysis. The service provider may generate a message offering to provide prior authorization assistance and may insert or otherwise append the message to the adjudicated response and may transmit the adjudicated response and message to the healthcare provider (e.g., pharmacy) who initiated the healthcare claim transaction. The healthcare provider and/or patient may then determine if they want to accept the offer of prior authorization assistance from the service provider.

If they wish to accept the offer of prior authorization assistance, the healthcare provider may submit a second healthcare claim transaction. In one example the second healthcare claim transaction may be a resubmission of the original healthcare claim transaction. Furthermore, as the second healthcare claim transaction is for the same patient and prescription and is from the same healthcare provider, much (but not all) of the data in the second healthcare transaction will be the same.

The service provider may receive and evaluate the second healthcare claim transaction prior and/or subsequent to routing or otherwise communicating the second healthcare claim transaction to a claims processor. The service provider may transmit the second healthcare claim transaction to a claims processor for adjudication and receive back from the claims processor a second adjudicated response. The service provider may determine if the second transaction was approved and if not, the basis for rejecting the second transaction. The service provider may further determine if the second healthcare claim transaction was rejected for lack of prior authorization. If rejected for lack of prior authorization, the service provider may compare one or more of the data elements in the second transaction to data elements for stored, previously submitted healthcare transactions to determine if a match exists. If a matching record for a stored, previously submitted healthcare transaction is identified, the service provider may determine the time/date that each of the second healthcare claim transaction and matching healthcare transaction were submitted to the service provider and may calculate the difference in those submission times. The service provider may then compare the submission time difference to a time limit threshold to determine if the submission time difference satisfies the time limit threshold.

If the submission time difference satisfies the time limit threshold, the service provider may presume, or otherwise infer, that the second healthcare claim transaction is a request for prior authorization assistance, even though nothing in the second healthcare claim transaction makes such a request (even via code). The service provider may store the data from the second healthcare claim transaction and generate an approval message notifying the healthcare provider and/or patient, that the request for prior authorization assistance has been accepted. The service provider may insert or otherwise append the approval message to the second adjudicated response and may send that to the healthcare provider. The service provider may also prepare the data necessary for the prior authorization and may send that to a prior authorization assistance computer.

System Overview

FIG. 1 illustrates an example system 100 supporting healthcare transactions, electronic prescription ordering activities, and prescription billing activities according to one example embodiment. The exemplary system 100 facilitates the determination as to whether a request for prior authorization assistance is being made by a healthcare provider based on an evaluation of the data in the healthcare transaction as part of or in-line with the processing of healthcare transactions and will now be described illustratively with respect to FIG. 1. As shown in FIG. 1, the system 100 may include at least one healthcare provider computer 104, at least one service provider computer 106, a prior authorization logic module 180, and at least one claims processor computer 108.

As desired, each of the healthcare provider computer 104, service provider computer 106, prior authorization logic module 180, and/or claims processor computer 108 may include one or more processing devices that may be configured for accessing and reading associated computer-readable media having stored thereon data and/or computer-executable instructions for implementing the various methods disclosed in the exemplary embodiments discussed herein.

Additionally, in certain exemplary embodiments, the service provider computer 106 and/or the prior authorization logic module 180 may be in communication with one or more data storage devices, such as rejected claims database 182. The rejected claims database 182 may receive, store, and provide, as needed, healthcare transactions data from the service provider computer 106 and/or the prior authorization logic module 180. In certain exemplary embodiments, the healthcare transactions data includes all or any portion of the data included in healthcare transactions received by the service provider computer 106 from a healthcare provider computer 104 and/or rejected by a claims processor due to a prior authorization requirement. In addition, the rejection claims database 182 or another database may include time threshold limits, schedules, tables or listings of healthcare providers or claims processors for which certain data, such as prescriber phone numbers, are removed from healthcare transactions before forwarding the transactions to a claims processor computer, tables, schedules or listings of records that include prescriber contact information and, optionally, a date that the contact information was last verified with a claims processor or healthcare provider, etc. Alternatively, the data storage function may be included in the service provider computer 106 and/or the prior authorization logic module 180 itself, such as in the memory 142 of the service provider computer 106.

Generally, network devices and systems, including one or more of the healthcare provider computer 104, service provider computer 106, prior authorization logic module 180, and claims processor computer 108 may include or otherwise be associated with suitable hardware and/or software for transmitting and receiving data and/or computer-executable instructions over one or more communications links or networks. These network devices and systems may also include any number of processors for processing data and executing computer-executable instructions, as well as other internal and peripheral components that are well known in the art. Further, these network devices and systems may include or be in communication with any number of suitable memory devices operable to store data and/or computer-executable instructions. By executing computer-executable instructions, each of the network devices may form a special purpose computer or particular machine. As used herein, the term "computer-readable medium" describes any form of suitable memory or memory device.

As shown in FIG. 1, the healthcare provider computer 104, service provider computer 106, claims processor computer 108, prior authorization logic module 180, and rejected claims database 182 may be in communication with each other via one or more networks, such as network 110, which as described below can include one or more separate or shared private and public networks, including the Internet or a publicly switched telephone network. Each of these components, the healthcare provider computer 104, service provider computer 106, claims processor computer 108, prior authorization logic module 180, rejected claims database 182, and the network 110 will now be discussed in further detail.

Each healthcare provider computer 104 may be associated with (e.g., located within and/or providing computing services for) a healthcare provider, such as, for example, a pharmacy, physician's office, hospital, clinic, etc. While the exemplary healthcare provider computer 104 will be described as within or part of a pharmacy or pharmacy network with regard to the methods of FIGS. 3A-5B, this is for example only and is not intended to be limiting in any manner. Each healthcare provider computer 104 may be any suitable processor-driven device that facilitates the processing of healthcare requests made by patients or consumers and the communication of information associated with healthcare transactions to the service provider computer 106, such as a server computer, a mainframe computer, one or more networked computers, a desktop computer, a personal computer, a digital assistant, a personal digital assistant, a digital tablet, an Internet appliance, an application-specific circuit, microcontroller, minicomputer, or any other processor-based device. In certain embodiments, each healthcare provider computer 104 may be a suitable point-of-sale device associated with a healthcare provider. The execution of the computer-implemented instructions by the healthcare provider computer 104 may form a special purpose computer or other particular machine that is operable to facilitate the processing of healthcare requests made by patients and the communication of information associated with healthcare transactions to a service provider computer 106. Additionally, in certain example embodiments, the operations and/or control of each healthcare provider computer 104 may be distributed amongst several processing components.

In addition to having one or more processors 124, each healthcare provider computer 104 may include one or more memory devices 126, one or more input/output ("I/O") interfaces 128, and one or more network interfaces 130. The memory devices 126 may be any suitable memory device, for example, caches, read-only memory devices, random access memory devices, magnetic storage devices, removable storage devices, etc. The memory devices 126 may store data, executable instructions, and/or various program modules utilized by the healthcare provider computer 104, for example, data files 132, an operating system ("OS") 134, and/or a client module 138, respectively. The data files 132 may include any suitable data that facilitates the receipt and/or processing of healthcare requests by the healthcare provider computer 104 and the generation and/or processing of healthcare transactions that are communicated to the service provider computer 106. For example, the data files 132 may include, but are not limited to, healthcare information and/or contact information associated with one or more patients, information associated with the particular healthcare provider and/or the respective healthcare provider computer 104, information associated with the service provider computer 106, information associated with one or more claims processors, and/or information associated with one or more healthcare transactions. The OS 134 may be any suitable software module that controls the general operation of the healthcare provider computer 104. The OS 134 may also facilitate the execution of other software modules by the one or more processors 124, for example, the client module 138. The OS 134 may be any currently existing or future-developed operating system including, but not limited to, Microsoft Windows®, Apple OSX™, Linux, Unix, or a mainframe operating system.

The client module 138 may be an Internet browser or other suitable software, including a dedicated program, for interacting with the service provider computer 106. For example, a user 120 such as a pharmacist, pharmacy assistant, nurse practitioner, physician, nurse, or other pharmacy, hospital, physician's office, or other healthcare provider employee may utilize the client module 138 in preparing and transmitting a healthcare transaction, such as a predetermination of benefits transaction, healthcare claim transaction, prescription claim or billing request, healthcare order transaction, or e-prescription transaction (e.g., electronic prescription order transaction, e-script, or e-prescription), to the service provider computer 106 for delivery to the appropriate claims processor computer 108 or other third-party for adjudication or other coverage/benefits determination. The healthcare provider computer 104 may also utilize the client module 138 to retrieve or otherwise receive data, messages, or responses from the service provider computer 106 and/or other components of the system 100. For example, in certain example embodiments, the client module 138 may be utilized to receive a rejection of the healthcare transaction and/or an adjudicated healthcare transaction from the service provider computer 106 as will be described below.

The one or more I/O interfaces 128 may facilitate communication between the healthcare provider computer 104 and one or more input/output devices, for example, one or more user interface devices, such as, a display, keypad, keyboard, control panel, touch screen display, remote control, mouse, microphone, etc. that facilitate user interaction with the healthcare provider computer 104. For example, the one or more I/O interfaces 128 may facilitate entry of information associated with a healthcare transaction by an employee 120 of a healthcare provider, such as a pharmacy employee, pharmacist, physician, nurse, hospital employee, or nurse practitioner affiliated with a pharmacy, hospital, physician's office or other similar healthcare provider. The one or more network interfaces 130 may facilitate connection of the healthcare provider computer 104 to one or more suitable networks, for example, the network 110 illustrated in FIG. 1. In this regard, the healthcare provider computer 104 may receive and/or communicate information to other network components of the system 100, such as the service provider computer 106.

With continued reference to FIG. 1, the service provider computer 106 may include, but is not limited to, any suitable processor-driven device that is configured for receiving, processing, and fulfilling requests from the one or more healthcare provider computers 104, the prior authorization logic module 180, the rejected claims database 182, and/or the claims processor computer 108 relating to pharmacy, benefits, billing, electronic prescription submission, and/or other healthcare transactions and/or other activities. In certain exemplary embodiments, the service provider computer 106 may be a switch/router that routes healthcare transactions and/or other healthcare requests from a pharmacy to a claims processor or from a physician or hospital to a pharmacy. For example, the service provider computer 106 may route predetermination of benefits transactions and healthcare claim transactions communicated from the healthcare provider computer 104 (at e.g., a pharmacy) to a claims processor computer 108, such as a pharmacy benefits manager (PBM), an insurer, a Medicare payor, other governmental healthcare insurance payor, or other third-party payor.

In certain embodiments, the service provider computer 106 may include a suitable host server, host module, or other software that facilitates the receipt of a healthcare transaction from a healthcare provider computer 104 and/or the routing of the received healthcare transaction to a claims processor computer 108. Any number of healthcare provider computers 104, prior authorization logic modules 180, rejected claims databases 182, and/or claims processor computers 108 may be in communication with the service provider computer 106, via the network 110 for example, as desired in various embodiments.

The service provider computer 106 may include any number of special purpose computers or other particular machines, application-specific circuits, microcontrollers, personal computers, minicomputers, mainframe computers, servers, networked computers, and/or other processor-driven devices. In certain embodiments, the operations of the service provider computer 106 may be controlled by computer-executed or computer-implemented instructions that are executed by one or more processors 140 associated with the service provider computer 106 to form a special purpose computer or other particular machine that is operable to facilitate the receipt, routing, and/or processing of healthcare transactions. The one or more processors 140 that control the operations of the service provider computer 106 may be incorporated into the service provider computer 106 and/or in communication with the service provider computer 106 via one or more suitable networks. In certain exemplary embodiments, the operations and/or control of the service provider computer 106 may be distributed amongst several processing components.

Similar to the healthcare provider computer 104 described above, the service provider computer 106 may include one or more processors 140, one or more memory devices 142, one or more input/output ("I/O") interfaces 144, and one or more network interfaces 146. The one or more memory devices 142 may be any suitable memory devices, for example, caches, read only memory devices, random access memory devices, magnetic storage devices, removable memory devices, etc. The one or more memory devices 142 may store data, executable instructions, and/or various program modules utilized by the service provider computer 106, for example, data files 148, an operating system ("OS") 150, the host module 154, a service provider module 156, and a database management system ("DBMS") 152 to facilitate management of data files 148 and other data stored in the memory devices 142. The OS 150 may be a suitable software module that controls the general operation of the service provider computer 106 and/or that facilitates the execution of other software modules. The OS 150 may be any currently existing or future-developed operating system including, but is not limited to, Microsoft Windows®, Apple OSX™, Linux, Unix, or a mainframe operating system.

The service provider module 156 may be operable to perform one or more pre-edits or pre-analysis on a received healthcare transaction prior to routing or otherwise communicating the received healthcare transaction, such as a healthcare claim transaction, to a suitable claims processor computer 108 or an e-prescription transaction to a suitable pharmacy/healthcare provider computer 104. Additionally, the service provider module 156 may be operable to perform one or more post-edits on an adjudicated reply or response that is received from a claims processor computer 108 for a healthcare transaction prior to routing the adjudicated response to one of the healthcare provider computers 104. Further, the service provider module 156 may be operable to receive and evaluate the healthcare transaction to determine if the transaction was rejection based on a need for prior authorization or is the filing of the transaction was an implied request for prior authorization assistance from a healthcare provider associated with the healthcare provider computer 104 prior to or after routing the transaction to a claims processor computer 108 for adjudication. In yet other example embodiments, the service provider module 156 may be operable to compare information from previous healthcare transactions with information in a current healthcare transaction to determine if the information in the current healthcare transaction matches the information/data in a stored transaction and may evaluate and retrieve the data from any matching transactions. In certain example embodiments, the service provider module 156 may also be operable to perform the functions described with references to the prior authorization logic module 180 herein. A wide variety of different pre-edits and/or post-edits may be performed by the service provider module 156 as desired in various embodiments of the disclosure.

According to one exemplary embodiment, the data files 148 may store healthcare transaction records associated with communications received from various healthcare provider computers 104 and/or various claims processor computers 108. The data files 148 may also store any number of suitable routing tables that facilitate determining the destination of communications received from a healthcare provider computer 104 or claims processor computer 108. In certain example embodiments, the data discussed herein that is included in the rejected claims database 182 may alternatively be stored and accessed from the data files 148. The exemplary data files 148 may also store records containing, for example, patient identification data, healthcare transactions, tables identifying healthcare providers, the predetermined time threshold limits from which the receipt of healthcare transactions can be inferred as a request for prior authorization assistance.

The host module 154 may receive, process, and respond to requests from the client module 138 of the healthcare provider computer 104, may receive, process, and respond to requests of the prior authorization logic module 180, and may further receive, process, and respond to requests of the host module 172 of the claims processor computer 108. The service provider computer 106 may include additional program modules for performing other processing methods described herein. Those of ordinary skill in the art will appreciate that the service provider computer 106 may include alternate and/or additional components, hardware or software without departing from exemplary embodiments of the disclosure.

With continued reference to the service provider computer 106, the one or more I/O interfaces 144 may facilitate communication between the service provider computer 106 and one or more input/output devices, for example, one or more user interface devices, such as a display, keypad, keyboard, mouse, control panel, touch screen display, remote control, microphone, etc. that facilitate user interaction with the service provider computer 106. The one or more network interfaces 146 may facilitate connection of the service provider computer 106 to one or more suitable networks, for example, the network 110 illustrated in FIG. 1. In this regard, the service provider computer 106 may communicate with other components of the system 100.

One or more prior authorization logic modules 180 may also be operative with or included with the service provider computer 106. The prior authorization logic module 180 may include computer-executable instructions for facilitating claim rejection resolution and/or prior authorization assistance. As an example, the prior authorization logic module 180 may be operative or configured to qualify healthcare transactions for eligibility for prior authorization assistance, and/or generate or provide, either alone or in conjunction with the service provider computer 106, a request for prior authorization assistance to a prior authorization assistance computer (not shown). Where needed, the prior authorization logic module 180 may store or record healthcare transaction records in a history file or other similar list/record structure of the database 182 to support the facilitation of prior authorization assistance. For example, the prior authorization logic module 180 may be operative or configured to match data from a received healthcare transaction from the healthcare provider computer 104 to a stored transaction history record of a prior claim transaction in order to determine if a request for prior authorization assistance is being made and to generate a request for prior authorization assistance for delivery to the prior authorization assistance computer. The prior authorization logic module 180 can likewise be configured to communicate information regarding statuses of prior authorization requests according to a variety of communications means, including via a transaction response, an Internet website/portal, email, facsimile, etc.

In one example embodiment, the prior authorization logic module 180 may be implemented as computer-implemented instructions of the memory 128 of the service provider computer 104. Alternatively, the prior authorization logic module 180 may also be implemented as computer-implemented instructions of a memory of a separate processor-based system, according to another example embodiment.

The rejected claims database 182 of FIG. 1 represents one or more databases that can be locally or remotely distributed with respect to the service provider computer 106 and/or the prior authorization logic module 180. The rejected claims database 182 may be operable to store information associated with various patients and/or from various healthcare transactions that have been received by the service provider computer 106 and/or rejected during the adjudication process by the claims processor computer 106 based on, for example, a need for prior authorization, for submitting a refill too soon, for submitting a request for a medication that is a duplicate therapy of another medication (e.g., another drug in the same class) that has not been completed, and other similar bases for rejection. The rejected claims database 182 may also store information from various healthcare transactions that have been approved during the adjudication process. The rejected claims database 182 may also store records of one or more insurers, government payors, Medicare Part D payors, accountable care organizations, claims clearinghouses, pharmacies or other healthcare providers for which prescriber phone numbers are to be removed from healthcare transactions prior to transmitting the transactions to the claims processor computer 108. The rejected claims database 182 may also store records of prescriber contact information and, optionally, a date that the contact information was last verified with a claims processor or healthcare provider. The patient, prescriber, time threshold limit, and healthcare transaction data in the database 182 may then be accessed and evaluated by the prior authorization logic module 180 and/or the service provider computer 106, such as by the service provider module 156.

With continued reference to FIG. 1, the claims processor computer 108 may be any suitable processor-driven device that facilitates receiving, processing, and/or fulfilling healthcare transactions, such as predetermination of benefits transactions, healthcare claim transactions, prescription claim or billing requests, healthcare order transactions, or e-prescription transactions (e.g., electronic prescription order transactions, e-scripts, or e-prescriptions) received from the service provider computer 106. For example, the claims processor computer 108 may be a processor-driven device associated with one or more PBMs, insurers, government payors, Medicare Part D payors, accountable care organizations, or claims clearinghouses. As desired, the claims processor computer 108 may include any number of special purpose computers or other particular machines, application-specific circuits, microcontrollers, personal computers, minicomputers, mainframe computers, servers, and the like.

In certain exemplary embodiments, the operations of the claims processor computer 108 may be controlled by computer-executed or computer-implemented instructions that are executed by one or more processors associated with the claims processor computer 108 to form a special purpose computer or other particular machine that is operable to facilitate the receipt, processing, and/or fulfillment of healthcare transactions received from the service provider computer 106. The one or more processors that control the operations of the claims processor computer 108 may be incorporated into the claims processor computer 108 and/or in communication with the claims processor computer 108 via one or more suitable networks. In certain embodiments, the operations and/or control of the claims processor computer 108 may be distributed amongst several processing components.

Similar to other components of the system 100, the claims processor computer 108 may include one or more processors 158, one or more memory devices 160, one or more input/output ("I/O") interfaces 162, and one or more network interfaces 164. The one or more memory devices 160 may be any suitable memory devices, for example, caches, read-only memory devices, random access memory devices, magnetic storage devices, removable memory devices. The one or more memory devices 160 may store data, executable instructions, and/or various program modules utilized by the claims processor computer 108, for example, data files 166, an operating system ("OS") 168, a database management system ("DBMS") 170, and a host module 172. The data files 166 may include any suitable information that is utilized by the claims processor computer 108 to process healthcare transactions, for example, patient profiles, patient insurance information, other information associated with a patient, information associated with a healthcare provider, etc. The operating system OS 168 may be a suitable software module that controls the general operation of the claims processor computer 108. The OS 168 may also facilitate the execution of other software modules by the one or more processors 158, for example, the DBMS 170 and/or the host module 172. The OS 168 may be any currently existing or future-developed operating system including, but is not limited to, Microsoft Windows®, Apple OSX™, Linux, Unix, or a mainframe operating system.

The DBMS 170 may be a suitable software module that facilitates access and management of one or more databases that are utilized to store information that is utilized by the claims processor computer 108 in various example embodiments. The host module 172 may initiate, receive, process, and/or respond to requests, such as healthcare transactions or claim requests, from the host module 154 of the service provider computer 106. The claims processor computer 108 may include additional program modules for performing other pre-processing or post-processing methods described herein. Those of ordinary skill in the art will appreciate that the claims processor computer 108 may include alternate and/or additional components, hardware or software without departing from the example embodiments described herein.

The one or more I/O interfaces 162 may facilitate communication between the claims processor computer 108 and one or more input/output devices, for example, one or more user interface devices, such as a display, keypad, keyboard, mouse, control panel, touch screen display, remote control, microphone, etc. that facilitate user interaction with the claims processor computer 108. The one or more network interfaces 164 may facilitate connection of the claims processor computer 108 to one or more suitable networks, for example, the network 110. In this regard, the claims processor computer 108 may receive healthcare transactions and/or other communications from the service provider computer 106 and the claims processor computer 108 may communicate information associated with processing the healthcare transactions to the service provider computer 106.

The network 110 may include any telecommunication and/or data network, whether public, private, or a combination thereof, including a local area network, a wide area network, an intranet, the Internet, intermediate hand-held data transfer devices, and/or any combination thereof and may be wired and/or wireless. The network 110 may also allow for real-time, off-line, and/or batch transactions to be transmitted between or among the healthcare provider computer 104, the service provider computer 106, the prior authorization logic module 180, the rejected claims database 182, and/or the claims processor computer 108. Due to network connectivity, various methodologies, as described herein may be practiced in the context of distributed computing environments. Although the service provider computer 106 is shown for simplicity as being in communication with the healthcare provider computer 104, the prior authorization logic module 180, the rejected claims database 182, and/or the claims processor computer 108 via one intervening network 110, it is to be understood that any other network configuration is possible. For example, intervening network 110 may include a plurality of networks, each with devices such as gateways and routers for providing connectivity between or among networks 110. Instead of or in addition to a network 110, dedicated communication links may be used to connect the various devices in accordance with an example embodiment. For example, the service provider computer 106 may form the basis of network 110 that interconnects one or more of the healthcare provider computer 104, the prior authorization logic module 180, the rejected claims database 182, and the claims processor computer 108.

Those of ordinary skill in the art will appreciate that the system 100 shown in and described with respect to FIG. 1 is provided by way of example only. Numerous other operating environments, system architectures, and device configurations are possible. Other system embodiments can include fewer or greater numbers of components and may incorporate some or all of the functionality described with respect to the system components shown in FIG. 1. For example, in one exemplary embodiment, the service provider computer 106 (or other computer) may be implemented as a specialized processing machine that includes hardware and/or software for performing the methods described herein. Accordingly, the exemplary embodiments described herein should not be construed as being limited to any particular operating environment, system architecture, or device configuration.

Operational Overview

Figure 2A:
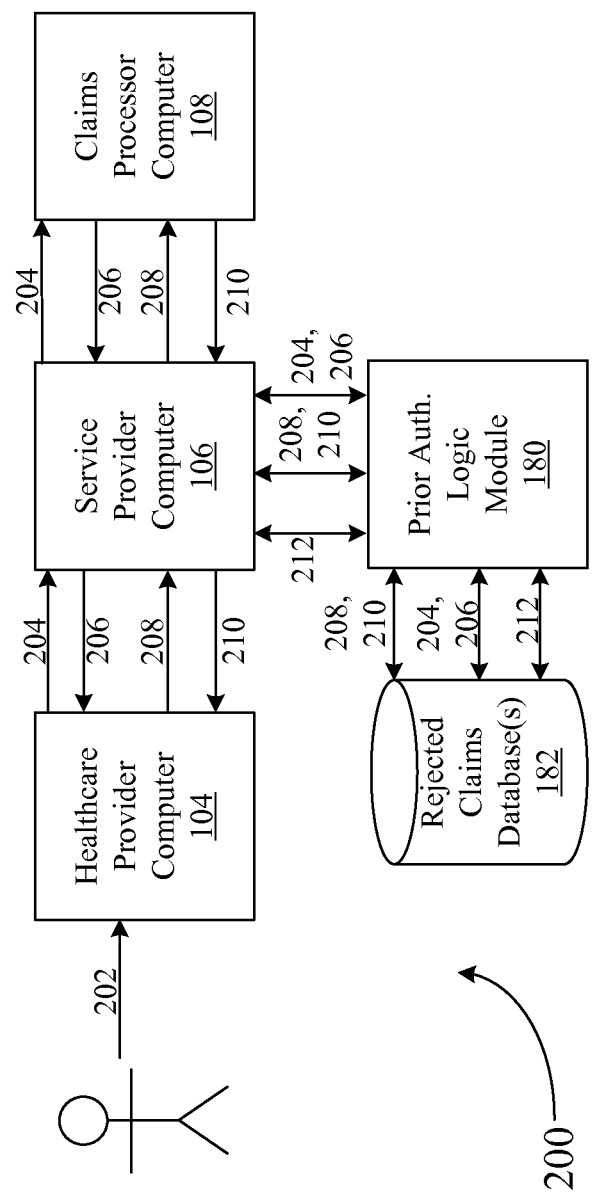
FIG. 2A is a diagram of an example data flow for determining if a healthcare provider is making a request for prior authorization assistance based on an evaluation of the data in the healthcare transaction and as part of the processing of a healthcare transaction processed through a service provider according to one exemplary embodiment.
Figure 3A:
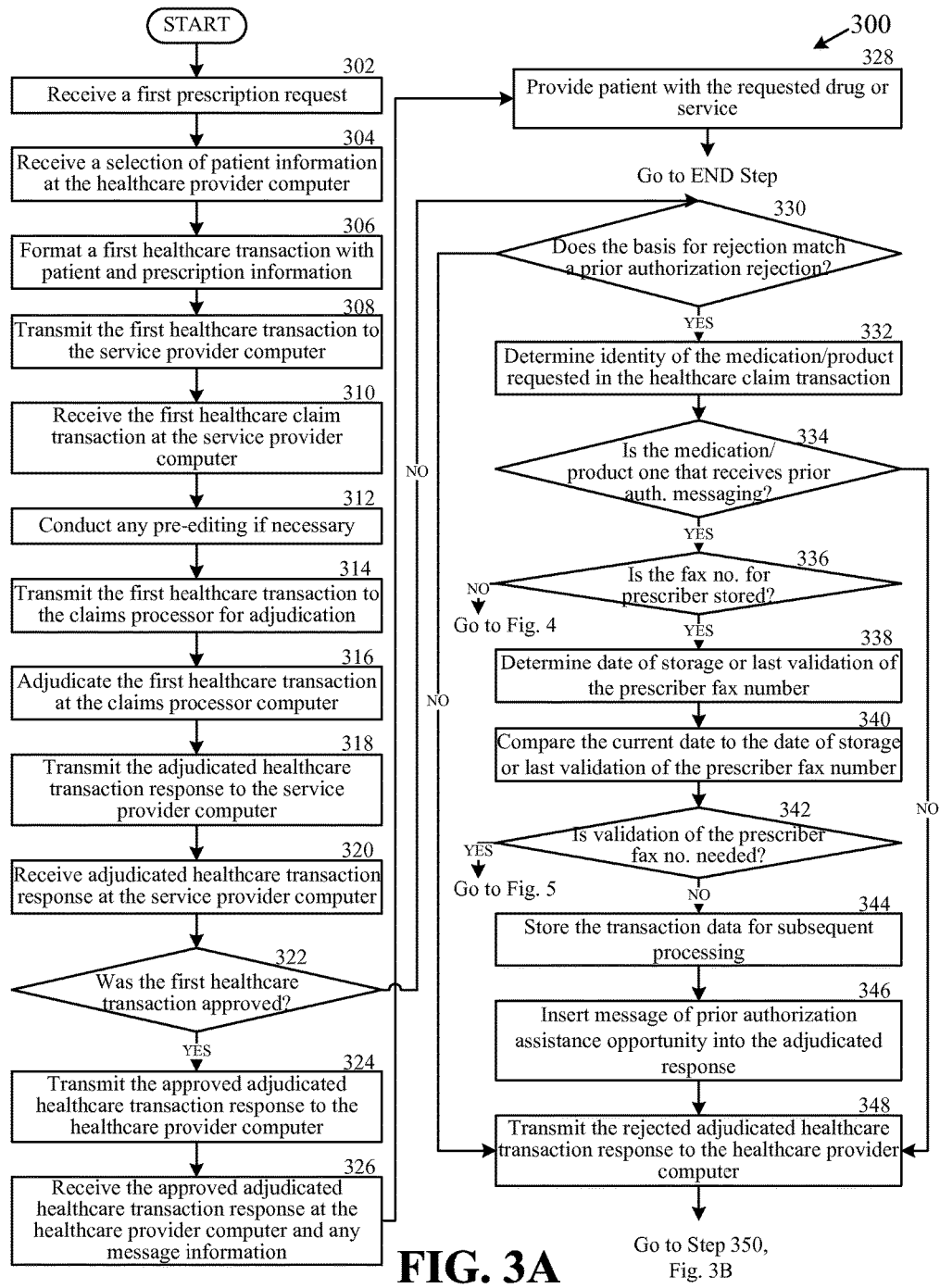
FIGS. 3A and 3B are a flow chart of an example method for determining if a healthcare provider is making a request for prior authorization assistance based on an evaluation of the data in the healthcare transaction and as part of the processing of a healthcare transaction, in accordance with one exemplary embodiment.
Figure 3B:
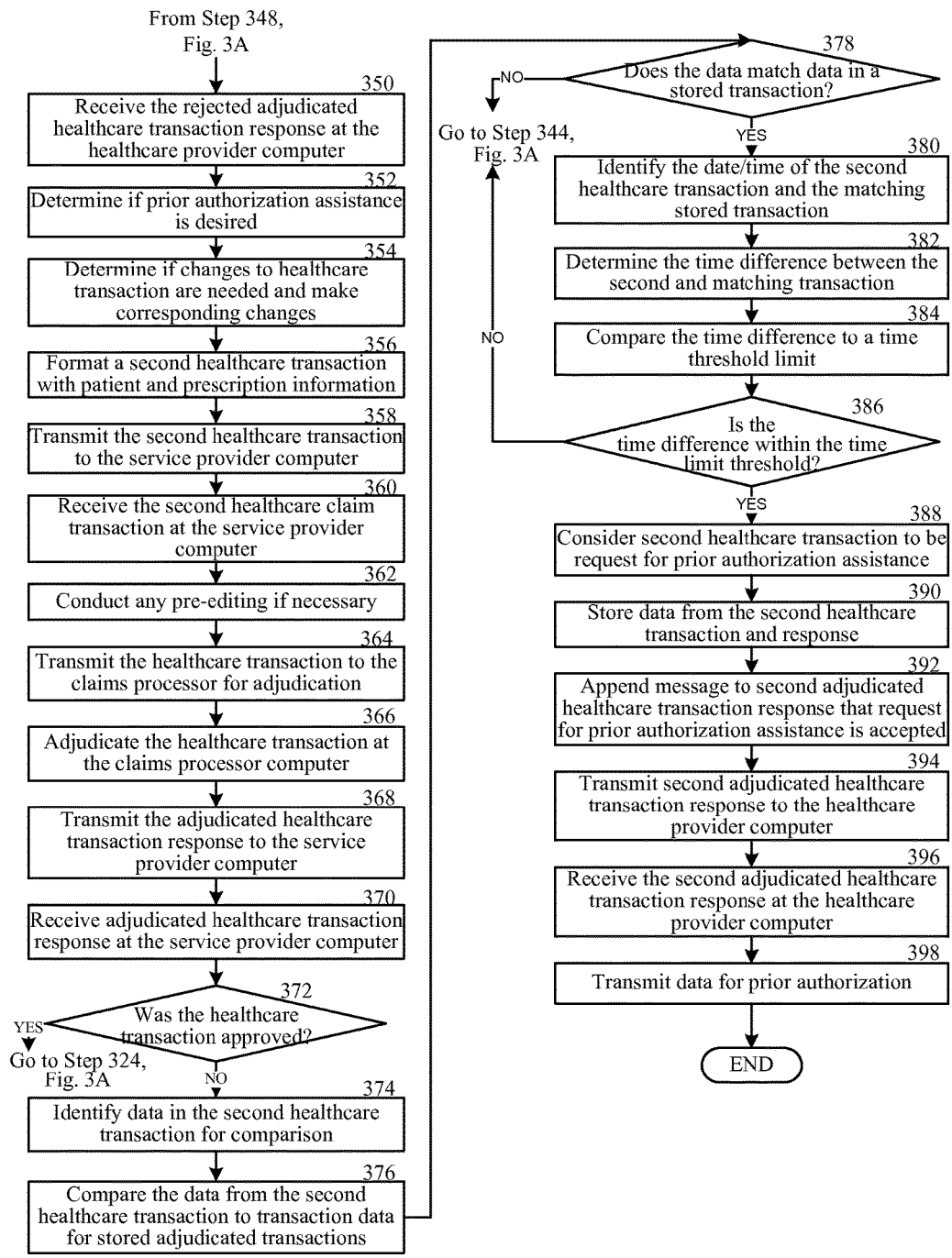

FIG. 2A is a diagram of one example data flow 200 for determining if a healthcare provider is making a request for prior authorization assistance based on an evaluation of the data in the healthcare transaction as part of or in-line with the processing of a healthcare transaction through a service provider, such as through the service provider computer 106 illustrated in FIG. 1. FIGS. 3A-3B are flow charts of an example method 300 for determining if a healthcare provider is making a request for prior authorization assistance based on an evaluation of the data in the healthcare transaction and as part of the processing of the healthcare transaction, such as a predetermination of benefits transaction, a healthcare claim transaction, prescription claim or billing request, healthcare order transaction, or e-prescription transaction (e.g., electronic prescription order transaction, e-script, or e-prescription), in accordance with one exemplary embodiment. The exemplary method 300, described below, may be performed by a suitable service provider computer 106 and/or prior authorization logic module 180. The exemplary methods 300-500 will be described with reference to a pharmacy as the healthcare provider; however, this is only for purposes of example as other healthcare providers could be substituted for, and should each be individually read as being a part of each of these methods. As such, where the discussion of the methods below and the drawings state a pharmacy, any other healthcare provider could be substituted, such as a physician, hospital, physician's office, clinic, prescriber of the medication, or healthcare center.

In addition, the exemplary methods 300-500 described below will be described with reference to a healthcare claim transaction as the healthcare transaction; however, this also is only for purposes of example as other healthcare transactions (which may include, for example, a predetermination of benefits transaction, the healthcare claim transaction, prescription claim or billing request, healthcare order transaction, or e-prescription transaction (e.g., electronic prescription order transaction, e-script, or e-prescription)) could be substituted for the healthcare claim transaction and each form of healthcare transaction should each individually be read as being used in the methods described below.

Referring now to FIGS. 1, 2A, 3A and 3B, the exemplary method 300 begins at the START step and proceeds to step 302, where a prescription request 202 is received. In one example embodiment, the prescription/order request 202 is received by a pharmacist at a pharmacy. The prescription/order request 202 may be received from a patient, another healthcare provider prescribing a medication or service (e.g., physician, hospital, etc.), by phone, via the Internet, via an electronic prescription or by way of an electronic system order. For example, the prescription 202 may be received by the patient from a prescriber of the medication, such as a doctor, dentist, nurse, physician's assistant, or any other person legally permitted to prescribe medication under applicable state and/or federal laws. The patient may go to the location of the pharmacy and physically hand the prescription request 202 to the pharmacist or make a request via a web portal communicably coupled to the healthcare provider computer 104 or an IVR communicably coupled to the healthcare provider computer 104. The pharmacist determines the patient's name and accesses the healthcare provider computer 104, which receives a selection of patient information from the pharmacist via the I/O interface 128 in step 304. For example, the pharmacist accesses the healthcare provider computer 104 (in this case a pharmacy computer, which may or may not be physically located at that pharmacy) and accesses a database of patient information, which may be stored in memory 126 or in another database either local or remote from the healthcare provider computer 104. The pharmacist can then select the name or other patient identification information in the patient information database that matches the name or other identification information of the patient.

In step 306, a first healthcare claim transaction 204 is generated and/or formatted at the healthcare provider computer 104. In certain exemplary embodiments, the healthcare provider computer 104 formats the first healthcare claim transaction 204 with patient information and prescription information. All or a portion of the information in the first healthcare claim transaction 204 can be input into the first healthcare claim transaction 204 by the pharmacist via the I/O interface 128. According to one example embodiment, the first healthcare claim transaction 204 may be formatted in accordance with a version of the National Council for Prescription Drug Programs (NCPDP) Telecommunication Standard, although other standards may be utilized as well. As desired, the first healthcare claim transaction 204 may include a Banking Identification Number (BIN Number) and/or a Processor Control Number (PCN) for identifying a particular claims processor computer (i.e., PBM, payor, insurance company, Medicare or other government healthcare insurance payor, accountable care organization, etc.), such as the claims processor computer 108, as a destination for the first healthcare claim transaction 204. In addition, the first healthcare claim transaction 204 may also include information relating to the patient, payor, prescriber, healthcare provider, and/or the requested medication/product/service. As an example, the first healthcare transaction 204 may include one or more of the following information:

Payor ID/Routing Information
BIN Number (i.e., Banking Identification Number), BIN Number and Processor Control Number (PCN), and/or BIN Number and Group ID that designates a destination of the healthcare transaction 204
Patient Information
Name (e.g., Patient Last Name, Patient First Name, etc.)
Date of Birth of Patient
Age of Patient
Gender
Patient Address (e.g., Street Address, Zip Code, etc.)
Patient Contact Information (e.g., patient telephone number, email address, etc.)
Patient Health Condition Information
Patient ID or other identifier
Insurance/Coverage Information
Cardholder Name (e.g., Cardholder First Name, Cardholder Last Name)
Cardholder ID and/or other identifier (e.g., person code)
Group ID and/or Group Information
Prescriber Information
Primary Care Provider ID or other identifier (e.g., NPI code)
Primary Care Provider Name (e.g., Last Name, First Name)
Prescriber ID or other identifier (e.g., NPI code, DEA number)
Prescriber Name (e.g., Last Name, First Name)
Prescriber Contact Information (e.g., Telephone Number, Facsimile Number, Email Address, etc.)
Pharmacy or other Healthcare Provider Information (e.g., store name, chain identifier, etc.)
Pharmacy or other Healthcare Provider ID (e.g., NPI code)
Claim Information
Drug, service, or product identifier/information (e.g., name of the medication/product/service, National Drug Code (NDC) code, RxNorm code, etc.)
Prescription/Service Reference Number (e.g., a value assigned to the healthcare transaction by the healthcare provider's computer system to identify the healthcare transaction from other transactions submitted by the healthcare provider)
Date Prescription Written
Quantity Dispensed
Days' Supply
Diagnosis/Condition
Pricing information for the drug/service/product (e.g., network price, Usual & Customary price)
Number of Refills Authorized
One or more NCPDP Message Fields
One or more Drug Utilization (DUR) Codes
Date of Service (submission time) (may include both the date and the time the transaction was submitted to the network by the healthcare provider)

The first healthcare claim transaction 204 can be used to determine if the claims processor associated with the claims processor computer 106 approves or rejects payment coverage for medication being requested in the first healthcare claim transaction 204 and, if approved, the amount the claims processor will cover (or pay) for the medication being requested and how much the patient co-pay amount will be.

The healthcare provider computer 104 transmits the first healthcare claim transaction 204 to the service provider computer 106 in step 308. In step 310, the service provider computer 106 receives the first healthcare claim transaction 204. For example, the first healthcare claim transaction 204 can be transmitted by the healthcare provider computer 104 to the service provider computer 106 through the network 110. In step 312, the service provider computer 106 conducts any pre-editing, if necessary, on the first healthcare claim transaction 204. The pre-edits may include verifying, adding, and/or editing information included in the first healthcare claim transaction 204 prior to it being communicated to a claims processor computer 108. For example, the service provider computer 106 can parse the first healthcare claim transaction 204 to determine if the Patient ZIP/Postal Code was submitted and if it is valid.

In addition, the pre-editing of the healthcare claim transaction 204 may include a review of the contents of the transaction 204 and a determination of whether a prescriber phone number or other contact information needs to be removed from the first healthcare claim transaction 204. In certain example embodiments, it may be necessary to remove the prescriber phone number and/or other prescriber contact information as well as other information from the healthcare claim transaction 204 to satisfy HIPAA requirements that the transaction 204 have the minimum information necessary. In one example, the service provider module 156 or another portion of the service provider computer can identify the BIN, BIN and PCN, or BIN and Group ID in the first healthcare claim transaction and can compare it to a table, schedule, or listing of data/records for payors for which the prescriber phone number should be removed from the transaction 204. If a match to the listing or data/records is determined, the service provider module may modify the transaction 204 by removing the prescriber phone number. In an alternative embodiment, information other than the payor identifier (such as the pharmacy/pharmacist identifier) may be evaluated to determine if information should be "scrubbed" from the transaction 204.

The service provider computer 106 transmits the first healthcare claim transaction 204 to the claims processor computer 108 in step 314. For example, a first healthcare claim transaction 204 can be transmitted from the service provider computer 106 to the claims processor computer 108 via the network 110. The claims processor computer 108 receives and adjudicates the first healthcare claim transaction 204 in step 316 to determine if the patient has coverage, to determine to what extent the patient's coverage covers the requested medication/product/service identified in the transaction 204, and to generate an adjudication 206 as to whether the transaction 204 is approved or rejected. Typically, if the transaction 204 is approved, the adjudicated response 206 provides the amount of the cost of the medication that will be covered by the claims processor/payor and the patient co-pay and if rejected, the adjudicated response 206 provides the reason for the rejection (e.g., prior authorization required, patient not covered, medication not covered, etc.). Example adjudications can include, but are not limited to, accepted, approved, paid, captured, denied, and denied with request for additional information and resubmission. In certain exemplary embodiments, the adjudication can be input into a field of the first healthcare claim transaction 204 that is recognized by the service provider computer 106, prior authorization logic module 180, and/or the healthcare provider computer 104. In step 318, the claims processor computer 108 transmits the adjudicated first healthcare claim transaction response 206 to the service provider computer 106 via, for example, the network 110.

The service provider computer 106 receives the adjudicated first healthcare claim transaction response 206 from the claims processor computer 108 in step 320. In step 322, an inquiry is conducted to determine if the adjudicated first healthcare claim transaction response 206 indicates that the transaction was approved or paid. In one exemplary embodiment, the service provider computer 106, such as the service provider module 156, parses the adjudicated first healthcare claim transaction response 206 and identifies the code in the field associated with adjudication. The service provider computer 106 compares that identified code to a table of adjudication codes to identify a match that signifies the adjudicated response from the claims processor computer 108. If the adjudication is that the first healthcare claim transaction 204 is approved or paid, the YES branch is followed to step 324, where the service provider computer 106 transmits the approved adjudicated first healthcare claim transaction response 206 to the healthcare provider computer 104. In one exemplary embodiment, the adjudicated response 206 is transmitted to the healthcare provider computer 104 via the network 110. Alternatively, the adjudicated first healthcare claim transaction response 206 may be transmitted to a healthcare provider via phone (such as with an IVR system), facsimile transmission, email, short message service (SMS) text, and/or multimedia messaging service (MMS) text.

The approved adjudicated first healthcare claim transaction response 206 is received at the healthcare provider computer 104 or by the healthcare provider in step 326. The healthcare provider may provide the patient with the medication requested in the first healthcare claim transaction 206 upon receipt of any necessary patient co-pay in step 328. The process then continues to the END step.

Returning to the inquiry of step 322, if the first adjudicated healthcare claim transaction response code indicates a denial (also sometimes referred to as a rejection or reject code), the NO branch is followed to step 330, where an inquiry is conducted to determine if the reject code identifies the rejection as being a prior authorization rejection. The service provider computer 106, for example the service provider module 156, the prior authorization logic module 180 or another portion of the service provider computer 106 can parse the adjudicated first healthcare claim transaction response 206 to identify the adjudication code and compare that code to a table, schedule, or database of adjudication codes (e.g., in the rejected claims database 182 or the data files 148) to identify a match to one or more reject codes and determine the basis for the rejection, based on that match.

In certain exemplary embodiments, a prior authorization rejection is one where the PBM, insurance company, government healthcare insurance payor, accountable care organization, or other benefits payor initially blocks a patient's coverage for a prescribed medication and requires that the prescriber (e.g., a doctor, dentist, hospital, their subordinates or any other person legally permitted to prescribe medications, products and/or services, etc.) contact the payor (either the claims processor or a party associated with the claims processor) to provide additional information to the payor (typically as to why the patient needs the identified medication/product/service. For example, the payor may want to make sure what is being prescribed is what the doctor intended to prescribe, that a generic or other equivalent medication cannot be substituted for the prescribed medication, or that other alternative medications or therapies have been attempted or a reason given why they should not need to be attempted in this case.

If the prior authorization logic module 180 identifies a match that indicates the first healthcare claim transaction 204 was denied or rejected based on a requirement for prior authorization, the YES branch is followed to step 332, where the prior authorization logic module 180 or another portion of the service provider computer 106 determines the identity of the medication/product/service requested in the first healthcare claim transaction 204. In one exemplary embodiment, the prior authorization logic module 180 parses the adjudicated first healthcare claim transaction response 206 to determine an identifier for the requested medication/product/service in the adjudicated first response 180. For example, the identifier may be an NDC code, RxNorm code, medication/product/service name or a general description of the medication/product/service being requested.

In step 334, an inquiry is conducted to determine if the medication/product/service being requested in the transaction 204 is one for which prior authorization messaging is provided. In one example embodiment, the determination is made by the prior authorization logic module 180 or another portion of the service provider computer 106. For example, the prior authorization logic module 180 may compare the identifier for the medication/product/service being requested and identified in step 332 to a table, listing, or schedule of identifiers for medications/products/services that receive prior authorization messaging to determine if a match exists. If a match exists, it represents that prior authorization messaging services are provided for the medication/product/service identified. If a match is not identified and the medication/product/service does not receive prior authorization messaging, the NO branch is followed to step 348. Otherwise, the YES branch is followed to step 336.

In step 336, an inquiry is conducted to determine if the facsimile number for the prescriber of the medication/product/service in the transaction 204 is stored (for example in the rejected claims database 182) and accessible by the prior authorization logic module 180 and/or the service provider computer 106. For example, the prior authorization logic module 180 or another portion of the service provider computer 106 can parse the transaction 204 or response 206 and identify the prescriber identifier (e.g., NPI code, DEA number, prescriber name, etc.) in the transaction 204. The prior authorization logic module 180 can then compare the prescriber identifier to stored prescriber identifiers in, for example, the rejected claims database to identify and match. The prior authorization logic module 180 can then determine if the matching record includes a facsimile number or any other desired contact information (e.g., email address) for the identified prescriber. If the prescriber facsimile number or other desired contact information is not stored and is desired, the NO branch is followed to FIG. 4. On the other hand, if the prescriber fax number or other desired contact information is already stored in memory (e.g., the database 182), the YES branch is followed to step 338.

In step 338, a determination is made of the date that the fax number for the prescriber was stored or last validated. In one example embodiment, the determination can be made by the prior authorization logic module 180 or another portion of the service provider computer 106 by evaluating a date stored/validated value in the record/table containing the fax number or other contact information. In step 340, the prior authorization logic module 180 or another portion of the service provider computer 106 can compare the stored or last validated date to the current date to determine how long it has been since the fax number was stored or last validated.

In step 342, an inquiry is conducted to determine if the prescriber fax number needs to be validated. In one example embodiment, the determination can be made by the prior authorization logic module 180 or another portion of the service provider computer 106 comparing a threshold validation value to the determined length that it has been since the fax number or other contact information for the prescriber was stored or validated. If the determined length violates (e.g., is greater than or greater than or equal to) the threshold validation value, then validation of the prescriber fax number or other contact information is needed. If the prior authorization logic module determines that validation is needed, the YES branch may be followed to FIG. 5. Otherwise, the NO branch may be followed to step 344.

In step 344, the prior authorization logic module 180 or another portion of the service provider computer 106 stores all or a portion of the first healthcare claim transaction 204 or adjudicated response 206 or all or a portion of the information from the first healthcare claim transaction 204 or adjudicated response 206 for subsequent comparison (e.g., comparing data from subsequent transactions to the data for the first healthcare claim transaction stored). For example the prior authorization logic module 180 or another portion of the service provider computer 106 may store all or a portion of the first healthcare claim transaction 206 or adjudicated response 206 or its data in the rejected claims database 182. The stored information can include, but is not limited to, the BIN number, PCN, any or all of the Patient Information, Prescriber ID, Healthcare Provider ID, Drug, service or product/service identifier (e.g., NDC code or RxNorm number), Fill number, prescription/service number, quantity dispensed, days' supply, and the Date of Service from the transaction 204 or 206.

In step 346, the prior authorization logic module 180 or another portion of the service provider computer 106 can modify the adjudicated first healthcare claim transaction response 206 by inserting or otherwise appending thereto a message notifying of an opportunity for receiving prior authorization assistance. In one example embodiment, the message can be inserted into a text field of the adjudicated first response 206. In one example, the message can state "prior authorization assistance, sponsored by [INSERT SPONSOR NAME], available for this medication. Resubmit claim to initiate prior authorization processing. No prescriber fax # required." The process then continues to step 348.

In step 348, the service provider computer 106 transmits the adjudicated first healthcare claim transaction response 206, including the message and the basis for rejection, to the healthcare provider computer 104 via, for example, the network 110. The healthcare provider computer 104 for the pharmacy receives the rejected adjudicated first healthcare claim transaction response 206 in step 350. In step 352, the pharmacy/pharmacist and/or patient determine if they desire to receive prior authorization assistance. If they desire the assistance, pharmacy/pharmacist can generate a second healthcare claim transaction 208 without specifically making a request via the transaction or otherwise for prior authorization assistance.

The pharmacist accesses the healthcare provider computer 104, reviews the contents of the first healthcare claim transaction and determines if changes to the first healthcare claim transaction are needed, and if so, makes the corresponding changes to the healthcare transaction in step 354. For example, the pharmacist accesses the healthcare provider computer 104 and accesses a database of healthcare transaction information, including patient information, which may be stored in memory 126 or in another database either local or remote from the healthcare provider computer 104. The pharmacist can then make any necessary changes to the first healthcare claim transaction in preparation for resubmission of that first healthcare claim transaction as a second healthcare claim transaction. In an alternative embodiment, rather than resubmitting the first healthcare claim transaction, the pharmacist may create a new healthcare claim transaction, also referenced as a second healthcare claim transaction for submission to the service provider computer 106.

In step 356, the second healthcare claim transaction 208 is generated and/or formatted at the healthcare provider computer 104. In certain exemplary embodiments, the healthcare provider computer 104 formats the second healthcare claim transaction 208 with patient information and prescription information. For example, the information could substantially match the information in the first healthcare claim transaction 204. According to one example embodiment, the second healthcare claim transaction 208 may be formatted in accordance with a version of the National Council for Prescription Drug Programs (NCPDP) Telecommunication Standard, although other standards may be utilized as well. As desired, the second healthcare claim transaction 208 may include a BIN Number and/or PCN for identifying a particular claims processor computer 108, as a destination for the second healthcare claim transaction 208. In addition, the second healthcare claim transaction 208 may also include any of the types of information described with reference to the first healthcare claim transaction 204.

The healthcare provider computer 104 transmits the second healthcare claim transaction 208 to the service provider computer 106 in step 358. In step 360, the service provider computer 106 receives the second healthcare claim transaction 208. For example, the second healthcare claim transaction 208 can be transmitted by the healthcare provider computer 104 to the service provider computer 106 through the network 110. In step 362, the service provider computer 106 conducts any pre-editing, if necessary, on the second healthcare claim transaction 208. The pre-edits may include any of those edits described with reference to the first healthcare claim transaction 204.

The service provider computer 106 transmits the second healthcare claim transaction 208 to the claims processor computer 108 in step 364. For example, the second healthcare claim transaction 208 can be transmitted from the service provider computer 106 to the claims processor computer 108 via the network 110. The claims processor computer 108 receives and adjudicates the second healthcare claim transaction 208 in step 366 to determine if the patient has coverage, to determine to what extent the patient's coverage covers the requested medication/product/service identified in the transaction 208, and to generate a second adjudication 210 as to whether the transaction 208 is approved or rejected. Typically, if the transaction 208 is approved, the second adjudicated response 210 provides the amount of the cost of the medication that will be covered by the claims processor/payor and the patient co-pay and if rejected, the second adjudicated response 210 provides the reason for the rejection (e.g., prior authorization required, patient not covered, medication not covered, etc.) in the form of a reject code. In certain exemplary embodiments, the second adjudication 310 can be input into a field of the second healthcare claim transaction 308 that is recognized by the service provider computer 106, prior authorization logic module 180, and/or the healthcare provider computer 104. In step 368, the claims processor computer 108 transmits the adjudicated second healthcare claim transaction response 210 to the service provider computer 106 via, for example, the network 110.

The service provider computer 106 receives the adjudicated second healthcare claim transaction response 210 from the claims processor computer 108 in step 370. In step 372, an inquiry is conducted to determine if the adjudicated second healthcare claim transaction response 210 indicates that the transaction was approved or paid by parsing the adjudicated second healthcare claim transaction response 210 and identifying the code in the field associated with adjudication. The prior authorization logic module 180 or another portion of the service provider computer 106 compares that identified code to a table of adjudication codes to identify a match that signifies the adjudicated response from the claims processor computer 108. If the adjudication is that the second healthcare claim transaction 208 is approved or paid, the YES branch is followed to step 324. On the other hand, if the second adjudicated healthcare claim transaction response code indicates a denial (also sometimes referred to as a rejection or reject code), an inquiry is conducted to determine if the reject code identifies the rejection as being a prior authorization rejection. The service provider computer 106, for example the service provider module 156, the prior authorization logic module 180 or another portion of the service provider computer 106 can parse the adjudicated second healthcare claim transaction response 210 to identify the adjudication code and compare that code to a table, schedule, or database of adjudication codes (e.g., in the rejected claims database 182 or the data files 148) to identify a match to one or more reject codes and determine the basis for the rejection, based on that match. If the prior authorization logic module 180 identifies a match that indicates the second healthcare claim transaction 208 was denied or rejected based on a requirement for prior authorization, the NO branch is followed to step 374.

In step 374, the prior authorization logic module 180 or another portion of the service provider computer 106 identifies and/or selects data from the second healthcare claim transaction 208 or response 210 to be used for comparison. For example, any of the information/data included in the second healthcare claim transaction 208 or response 210 may be used for comparison purposes. In one example embodiment, the prior authorization logic module 180 may identify and/or retrieve one or more of the BIN Number, PCN, prescription/service number, fill number (i.e., the number of this refill (or first fill) of the requested medication/product), medication/product/service identifier (e.g., NDC code, RxNorm code or name), quantity dispensed (of the medication/product), days' supply, patient identifier, prescriber identifier, and pharmacy identifier (collectively the "transaction comparison data") in the second healthcare claim transaction 208 or response 210 to be used for comparison.

In step 376, the prior authorization logic module 180 or another portion of the service provider computer 106 can compare the transaction comparison data from the second healthcare claim transaction 208 or response 210 to a multitude or records for previously submitted healthcare claim transactions and/or adjudicated responses stored in, for example, the rejected claims database 182 to determine if the transaction comparison data matches the data in one or more records for previously submitted healthcare claim transactions and/or adjudicated responses. For example, a match could be a match of all of the transaction comparison data to the similar data in a stored record. As such, the prior authorization logic module 180 can attempt to identify the stored data (or data otherwise held in some form of memory) for a previously submitted healthcare claim transaction or adjudicated response that includes data that matches one or more of the BIN Number, PCN, prescription/service number, fill number, medication/product/service identifier, quantity dispensed, days' supply, patient identifier, prescriber identifier, and/or pharmacy identifier from the second healthcare claim transaction 208 or adjudicated response 210.

In step 378, an inquiry is conducted to determine if the transaction comparison data for the second healthcare claim transaction 208 or adjudicated response 210 matches the data in a stored healthcare transaction or adjudicated response. In one example embodiment, the determination may be made by the prior authorization logic module 180 or another portion of the service provider computer 106. For example, the prior authorization logic module 180 may determine that the data for the first healthcare claim transaction 204 and/or adjudicated response 206, stored in step 344, matches the transaction comparison data for the second healthcare claim transaction 208 or adjudicated response

210. If a determination is made that the transaction comparison data for the second healthcare claim transaction 208 or adjudicated response 210 does not match the data in a stored healthcare transaction or response, the NO branch is followed to step 344. On the other hand, if one or more records for stored transactions or adjudicated responses are found to be matching the transaction comparison data, the YES branch is followed to step 380.

In step 380, the prior authorization logic module 180 or another portion of the service provider computer 106 can identify the date and/or time that the second healthcare claim transaction 208 was submitted to the service provider computer 106 for processing and likewise can identify the date and/or time that the matching stored transaction or adjudicated response(s) was submitted to the service provider computer 106 for processing based on the data stored in that matching record. In one example embodiment, the date and/or time can be identified from the Date of Service data in the second healthcare claim transaction 208 or response 210 and the corresponding matching record for the stored data of the healthcare transaction or adjudicated response. The prior authorization logic module 180 or another portion of the service provider computer 106 can compare the date/time of submission of the second healthcare claim transaction 208 to the date/time of submission of the matching stored transaction to determine the time difference of submission between the second healthcare claim transaction 208 and the matching stored transaction in step 382. For example, if only the date is provided, the date of submission for the second healthcare transaction 208 can be compared to the date of submission of the matching stored transaction to determine if they were submitted on the same day, one day apart, two days apart, etc. In another example, if the time and date are provided in the Date of Service data, the date/time of submission for the second healthcare transaction 208 can be compared to the date/time of submission of the matching stored transaction to determine more precisely how far apart the submission was, down to the number of days, hours, minutes, and/or seconds difference in the submission time of the two transactions. For example, the submission time difference can be determined by subtracting the submission time for the matching stored transaction from the submission time of the second healthcare claim transaction 208.

In step 384, the prior authorization logic module 180 or another portion of the service provider computer 106 can compare the determined submission time difference to a time limit threshold to determine if the submission time difference is within (or otherwise satisfies) the time limit threshold. In one example, the time limit threshold is a configurable amount of time that can be modified based on the desires of the user of the system. In certain embodiments, the time limit threshold may be the same day (especially when the Date of Service only provides a date and not a time), anywhere between 0-24 hours, or anywhere between 0-60 minutes. The time limit threshold can represent the difference in the amount of time where (when the submission time difference is less than or equal to the time limit threshold) it is believed that the submission of the second healthcare claim transaction 208 was done in response to an offer of assistance provided to the pharmacy (via the healthcare provider computer 104) in a prior adjudicated response (such as via the message inserted in step 346 above) and the submission of the second healthcare claim transaction 208 can be inferred as a request for that assistance, even though nothing in the second healthcare claim transaction 208 or adjudicated response 210 specifically makes that request. In one example embodiment, the offer for assistance can be an offer for prior authorization assistance. However, the time limit threshold may be similarly used to infer other requests for assistance, such as benefit investigation services, acceptance of a coupon/voucher offer, communication of data to a call center, or general acknowledgement that a message was received.

In step 386, an inquiry is conducted to determine if the submission time difference between the second healthcare claim transaction 208 and the matching transaction or adjudicated response is within the time limit threshold. In one example, the submission time difference is within the time limit threshold if it is less than or less than or equal to the time limit threshold. The determination can be made by the prior authorization logic module 180 or another portion of the service provider computer 106 and can be done by comparing the submission time difference to the time limit threshold. If the submission time difference is not within the time limit threshold, the NO branch can be followed to step 344. If the submission time difference is within (or otherwise satisfies) the time limit threshold, the YES branch can be followed to step 388.

In step 388, based at least on the fact that the transaction comparison data for the second healthcare claim transaction 208 or adjudicated response 210 matches a stored transaction or adjudicated response and the submission time difference between the two satisfies the time limit threshold, the prior authorization logic module 180 or another portion of the service provider computer 106 can infer or otherwise consider the second healthcare claim transaction 208 to be a request for prior authorization assistance, even though nothing in the second healthcare claim transaction 208 or adjudicated response 210 specifically makes that prior authorization assistance request and the request has not been otherwise made by the pharmacy/pharmacist or patient.

In step 390, the prior authorization logic module 180 or another portion of the service provider computer 106 stores all or a portion of the second healthcare claim transaction 208 or adjudicated response 210 or all or a portion of the information from the second healthcare claim transaction 208 or adjudicated response 210 for subsequent processing and/or comparisons. For example the prior authorization logic module 180 or another portion of the service provider computer 106 may store all or a portion of the second healthcare claim transaction 208 or adjudicated response 210 or its data in the rejected claims database 182. The stored information can include, but is not limited to, the BIN number, PCN, any or all of the Patient Information, Prescriber ID, Healthcare Provider ID, Drug, service or product/service identifier (e.g., NDC code or RxNorm number), Fill number, prescription/service number, quantity dispensed, days' supply, and the Date of Service from the transaction 208 or response 210.

In step 392, the prior authorization logic module 180 or another portion of the service provider computer 106 can modify the adjudicated second healthcare claim transaction response 210 by inserting or otherwise appending thereto a message notifying the pharmacy/pharmacist or patient that the request for prior authorization assistance has been accepted and the prior authorization assistance process has been initiated. The message may further include a request to resubmit the transaction 208 within a predetermined time period, such as 48 hours. In one example embodiment, the message can be inserted into a text field of the adjudicated second response 210.

In step 394, the service provider computer 106 transmits the adjudicated second healthcare claim transaction response 210, including the message and the basis for rejection, to the healthcare provider computer 104 via, for example, the network 110. The healthcare provider computer 104 for the pharmacy receives the adjudicated second healthcare claim transaction response 210 in step 396. In step 398, prior authorization logic module 180 or another portion of the service provider computer 106 may transmit a request for prior authorization assistance along with at least a portion of the data from the first or second healthcare claim transactions 204, 208 or adjudicated responses 206, 210 to a third-party prior authorization assistance computer via, for example, the network 110. The process then continues to the END step.

Figure 4A:
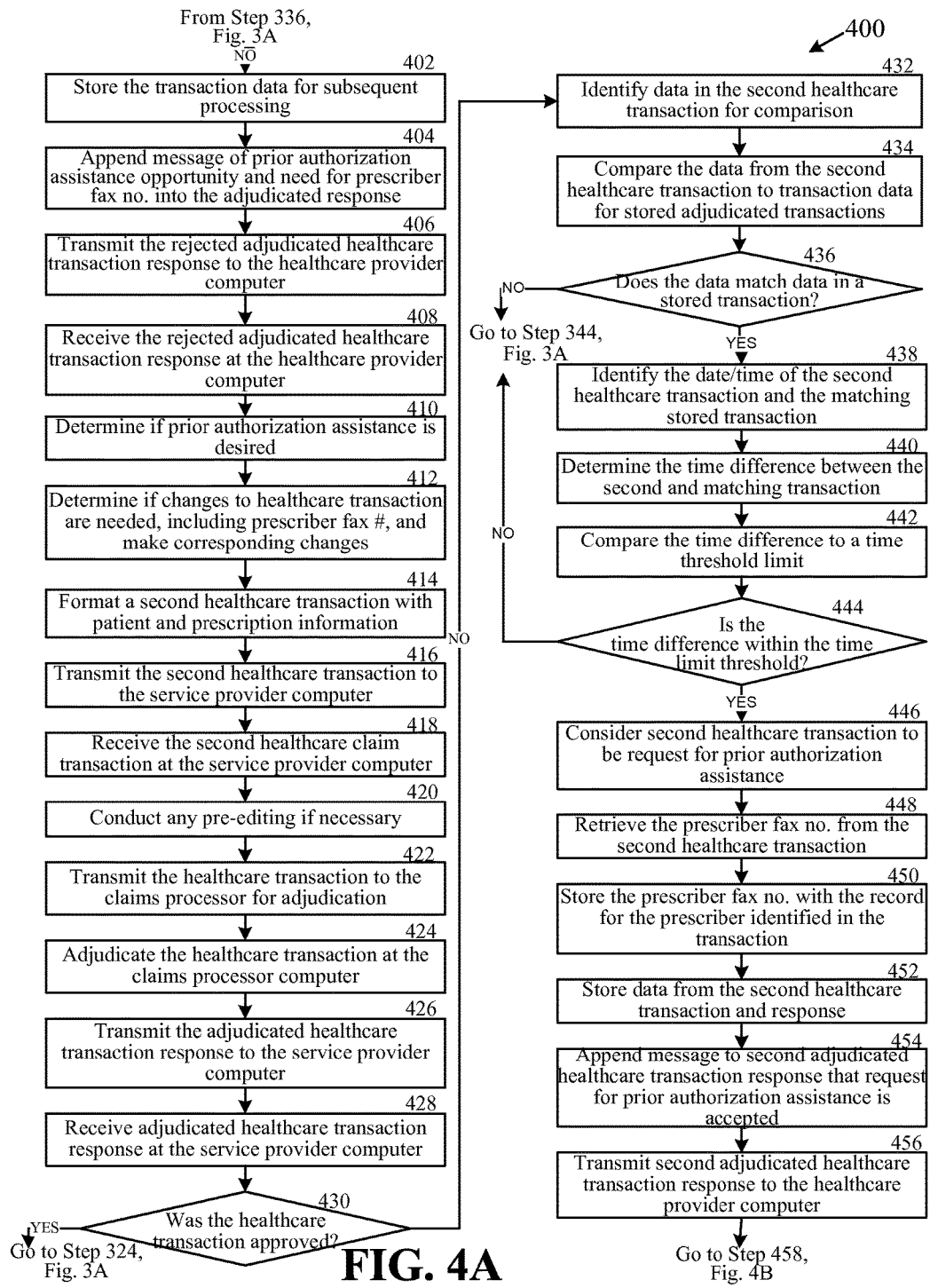
FIGS. 4A and 4B are a flow chart of an example method for determining if a healthcare provider is making a request for prior authorization assistance and obtaining contact information for a prescriber based on an evaluation of the data in the healthcare transaction and as part of the processing of a healthcare transaction, in accordance with one exemplary embodiment.
Figure 4B:
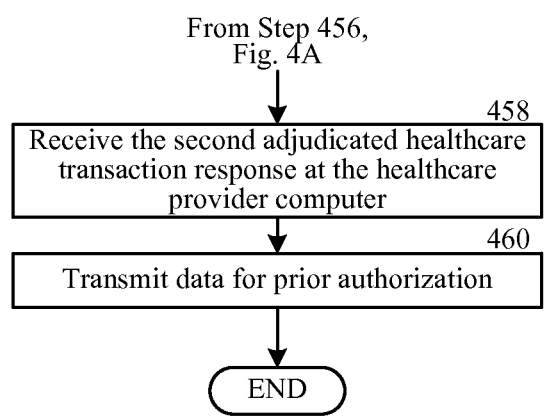

FIGS. 4A-4B are flow charts of an example method 400 for determining if a healthcare provider is making a request for prior authorization assistance and obtaining contact information for a prescriber based on an evaluation of the data in the healthcare transaction and as part of the processing of the healthcare transaction, such as a predetermination of benefits transaction, a healthcare claim transaction, prescription claim or billing request, healthcare order transaction, or e-prescription transaction (e.g., electronic prescription order transaction, e-script, or e-prescription), in accordance with one exemplary embodiment. The exemplary method 400, described below, may be performed by a suitable service provider computer 106 and/or prior authorization logic module 180. Referring now to FIGS. 1, 2A, 3A, 4A, and 4B, the exemplary method 400 may begin from the NO branch of the inquiry of step 336 of FIG. 3A upon a determination that the contact information (e.g., the prescriber fax number) for the prescriber that prescribed the medication/product/service in the first healthcare claim transaction 204 is not stored, for example, in the rejected claims database 182.

In step 402, the prior authorization logic module 180 or another portion of the service provider computer 106 stores all or a portion of the first healthcare claim transaction 204 or adjudicated response 206 or all or a portion of the information from the first healthcare claim transaction 204 or adjudicated response 206 for subsequent comparison. For example the prior authorization logic module 180 or another portion of the service provider computer 106 may store all or a portion of the first healthcare claim transaction 204 or adjudicated response 206 or its data in the rejected claims database 182. The stored information can include, but is not limited to, the BIN number, PCN, any or all of the Patient Information, Prescriber ID, Healthcare Provider ID, Drug, service or product/service identifier (e.g., NDC code or RxNorm number), Fill number, prescription/service number, quantity dispensed, days' supply, and the Date of Service from the transaction 204 or 206.

In step 404, the prior authorization logic module 180 or another portion of the service provider computer 106 can modify the adjudicated first healthcare claim transaction response 206 by inserting or otherwise appending thereto a message notifying of an opportunity for receiving prior authorization assistance and a need for the pharmacy/pharmacist to submit the prescriber fax number in the following response. In one example embodiment, the message can be inserted into a text field of the adjudicated first response 206. In one example, the message can state "prior authorization assistance, sponsored by [INSERT SPONSOR NAME], available for this medication. Enter prescriber FAX # in Intermediary Authorization ID field and resubmit claim to initiate prior authorization processing."

In step 406, the service provider computer 106 transmits the adjudicated first healthcare claim transaction response 206, including the message and the basis for rejection, to the healthcare provider computer 104 via, for example, the network 110. The healthcare provider computer 104 for the pharmacy receives the rejected adjudicated first healthcare claim transaction response 206 in step 408. In step 410, the pharmacy/pharmacist and/or patient determine if they desire to receive prior authorization assistance. If they desire the assistance, pharmacy/pharmacist can generate a second healthcare claim transaction 208 without specifically making a request via the transaction or otherwise for prior authorization assistance.

The pharmacist accesses the healthcare provider computer 104, reviews the contents of the first healthcare claim transaction and determines if changes to the first healthcare claim transaction are needed, and if so, makes the corresponding changes, including adding the prescriber fax number, if necessary, to the healthcare transaction in step 412. For example, the pharmacist can make any necessary changes to the first healthcare claim transaction in preparation for resubmission of that first healthcare claim transaction as a second healthcare claim transaction. In an alternative embodiment, rather than resubmitting the first healthcare claim transaction, the pharmacist may create a new healthcare claim transaction, also referenced as a second healthcare claim transaction for submission to the service provider computer 106.

In step 414, the second healthcare claim transaction 208 is generated and/or formatted at the healthcare provider computer 104. In certain exemplary embodiments, the healthcare provider computer 104 formats the second healthcare claim transaction 208 with patient information and prescription information. For example, the information could substantially match the information in the first healthcare claim transaction 204. The second healthcare claim transaction 208 may also include any of the types of information described with reference to the first healthcare claim transaction 204 and may further include the prescriber fax number, which may be positioned within the intermediary authorization ID field of the transaction 208.

The healthcare provider computer 104 transmits the second healthcare claim transaction 208 to the service provider computer 106 in step 416. In step 418, the service provider computer 106 receives the second healthcare claim transaction 208. In step 420, the service provider computer 106 conducts any pre-editing, if necessary, on the second healthcare claim transaction 208. The pre-edits may include any of those edits described with reference to the first healthcare claim transaction 204.

The service provider computer 106 transmits the second healthcare claim transaction 208 to the claims processor computer 108 in step 422 via the network 110. The claims processor computer 108 receives and adjudicates the second healthcare claim transaction 208 in step 424 to determine if the patient has coverage, to determine to what extent the patient's coverage covers the requested medication/product/service identified in the transaction 208, and to generate a second adjudication 210 as to whether the transaction 208 is approved or rejected. In step 426, the claims processor computer 108 transmits the adjudicated second healthcare claim transaction response 210 to the service provider computer 106 via, for example, the network 110.

The service provider computer 106 receives the adjudicated second healthcare claim transaction response 210 from the claims processor computer 108 in step 428. In step 430, an inquiry is conducted to determine if the adjudicated second healthcare claim transaction response 210 indicates that the transaction was approved or paid by parsing the adjudicated second healthcare claim transaction response 210 and identifying the code in the field associated with adjudication. The prior authorization logic module 180 or another portion of the service provider computer 106 compares that identified code to a table of adjudication codes to identify a match that signifies the adjudicated response from the claims processor computer 108. If the adjudication is that the second healthcare claim transaction 208 is approved or paid, the YES branch is followed to step 324 of FIG. 3A. On the other hand, if the second adjudicated healthcare claim transaction response code indicates a denial, an inquiry is conducted to determine if the reject code identifies the rejection as being a prior authorization rejection. The service provider computer 106, for example the service provider module 156, the prior authorization logic module 180 or another portion of the service provider computer 106 can parse the adjudicated second healthcare claim transaction response 210 to identify the adjudication code and compare that code to a table, schedule, or database of adjudication codes (e.g., in the rejected claims database 182 or the data files 148) to identify a match to one or more reject codes and determine the basis for the rejection, based on that match. If the prior authorization logic module 180 identifies a match that indicates the second healthcare claim transaction 208 was denied or rejected based on a requirement for prior authorization, the NO branch is followed to step 432.

In step 432, the prior authorization logic module 180 or another portion of the service provider computer 106 identifies and/or selects data from the second healthcare claim transaction 208 or response 210 to be used for comparison in a manner substantially the same as that described in step 374 of FIG. 3B. In step 434, the prior authorization logic module 180 or another portion of the service provider computer 106 can compare the transaction comparison data from the second healthcare claim transaction 208 or response 210 to a multitude of records for previously submitted healthcare claim transactions and/or adjudicated responses stored in, for example, the rejected claims database 182 to determine if the transaction comparison data matches the data in one or more records for previously submitted healthcare claim transactions and/or adjudicated responses in a manner substantially the same as that described in step 376 of FIG. 3B.

In step 436, an inquiry is conducted to determine if the transaction comparison data for the second healthcare claim transaction 208 or adjudicated response 210 matches the data in a stored healthcare transaction or adjudicated response. In one example embodiment, the determination may be made by the prior authorization logic module 180 or another portion of the service provider computer 106 in a manner substantially the same as that described in step 378 of FIG. 3B. If a determination is made that the transaction comparison data for the second healthcare claim transaction 208 or adjudicated response 210 does not match the data in a stored healthcare transaction or response, the NO branch is followed to step 344 of FIG. 3A. On the other hand, if one or more records for stored transactions or adjudicated responses are found to be matching the transaction comparison data, the YES branch is followed to step 438.

In step 438, the prior authorization logic module 180 or another portion of the service provider computer 106 can identify the date and/or time that the second healthcare claim transaction 208 was submitted to the service provider computer 106 for processing and likewise can identify the date and/or time that the matching stored transaction or adjudicated response(s) was submitted to the service provider computer 106 for processing based on the data stored in that matching record in a manner substantially the same as that described in step 380 of FIG. 3B. The prior authorization logic module 180 or another portion of the service provider computer 106 can compare the date/time of submission of the second healthcare claim transaction 208 to the date/time of submission of the matching stored transaction to determine the time difference of submission between the second healthcare claim transaction 208 and the matching stored transaction in step 440 in a manner substantially the same as that described in step 382 of FIG. 3B.

In step 442, the prior authorization logic module 180 or another portion of the service provider computer 106 can compare the determined submission time difference to a time limit threshold to determine if the submission time difference is within (or otherwise satisfies) the time limit threshold in substantially the same manner as that discussed in step 384 of FIG. 3B. In step 444, an inquiry is conducted to determine if the submission time difference between the second healthcare claim transaction 208 and the matching transaction or adjudicated response is within the time limit threshold. In one example, the submission time difference is within the time limit threshold if it is less than or less than or equal to the time limit threshold. The determination can be made by the prior authorization logic module 180 or another portion of the service provider computer 106 and can be done by comparing the submission time difference to the time limit threshold. If the submission time difference is not within the time limit threshold, the NO branch can be followed to step 344 of FIG. 3A. If the submission time difference is within (or otherwise satisfies) the time limit threshold, the YES branch can be followed to step 446.

In step 446, based at least on the fact that the transaction comparison data for the second healthcare claim transaction 208 or adjudicated response 210 matches a stored transaction or adjudicated response and the submission time difference between the two satisfies the time limit threshold, the prior authorization logic module 180 or another portion of the service provider computer 106 can infer or otherwise consider the second healthcare claim transaction 208 to be a request for prior authorization assistance, even though nothing in the second healthcare claim transaction 208 or adjudicated response 210 specifically makes that prior authorization assistance request and the request has not been otherwise made by the pharmacy/pharmacist or patient.

In step 448, the prior authorization logic module 180 or another portion of the service provider computer 106 can retrieve the prescriber fax number from the second healthcare claim transaction 208 or adjudicated response 210 and can store 214 the prescriber fax number with the record for the prescriber identified in the second healthcare claim transaction 208 in step 450. In one example, the prescriber fax number can be retrieved from the intermediary authorization ID field of the second healthcare claim transaction 208 and can be stored with the prescriber record in the rejected claims database 182, in memory 142, or in another database.

In step 452, the prior authorization logic module 180 or another portion of the service provider computer 106 stores all or a portion of the second healthcare claim transaction 208 or adjudicated response 210 or all or a portion of the information/data from the second healthcare claim transaction 208 or adjudicated response 210 for subsequent processing and/or comparisons. For example the prior authorization logic module 180 or another portion of the service provider computer 106 may store all or a portion of the second healthcare claim transaction 208 or adjudicated response 210 or its data in the rejected claims database 182.

In step 454, the prior authorization logic module 180 or another portion of the service provider computer 106 can modify the adjudicated second healthcare claim transaction response 210 by inserting or otherwise appending thereto a message notifying the pharmacy/pharmacist or patient that the request for prior authorization assistance has been accepted and the prior authorization assistance process has been initiated. The message may further include a request to resubmit the transaction 208 within a predetermined time period, such as 48 hours. In one example embodiment, the message can be inserted into a text field of the adjudicated second response 210.

In step 456, the service provider computer 106 transmits the adjudicated second healthcare claim transaction response 210, including the message and the basis for rejection, to the healthcare provider computer 104 via, for example, the network 110. The healthcare provider computer 104 for the pharmacy receives the adjudicated second healthcare claim transaction response 210 in step 458. In step 460, the prior authorization logic module 180 or another portion of the service provider computer 106 may transmit a request for prior authorization assistance along with at least a portion of the data from the first or second healthcare claim transactions 204, 208 or adjudicated responses 206, 210 to a third-party prior authorization assistance computer via, for example, the network 110. The process then continues to the END step.

Figure 5A:
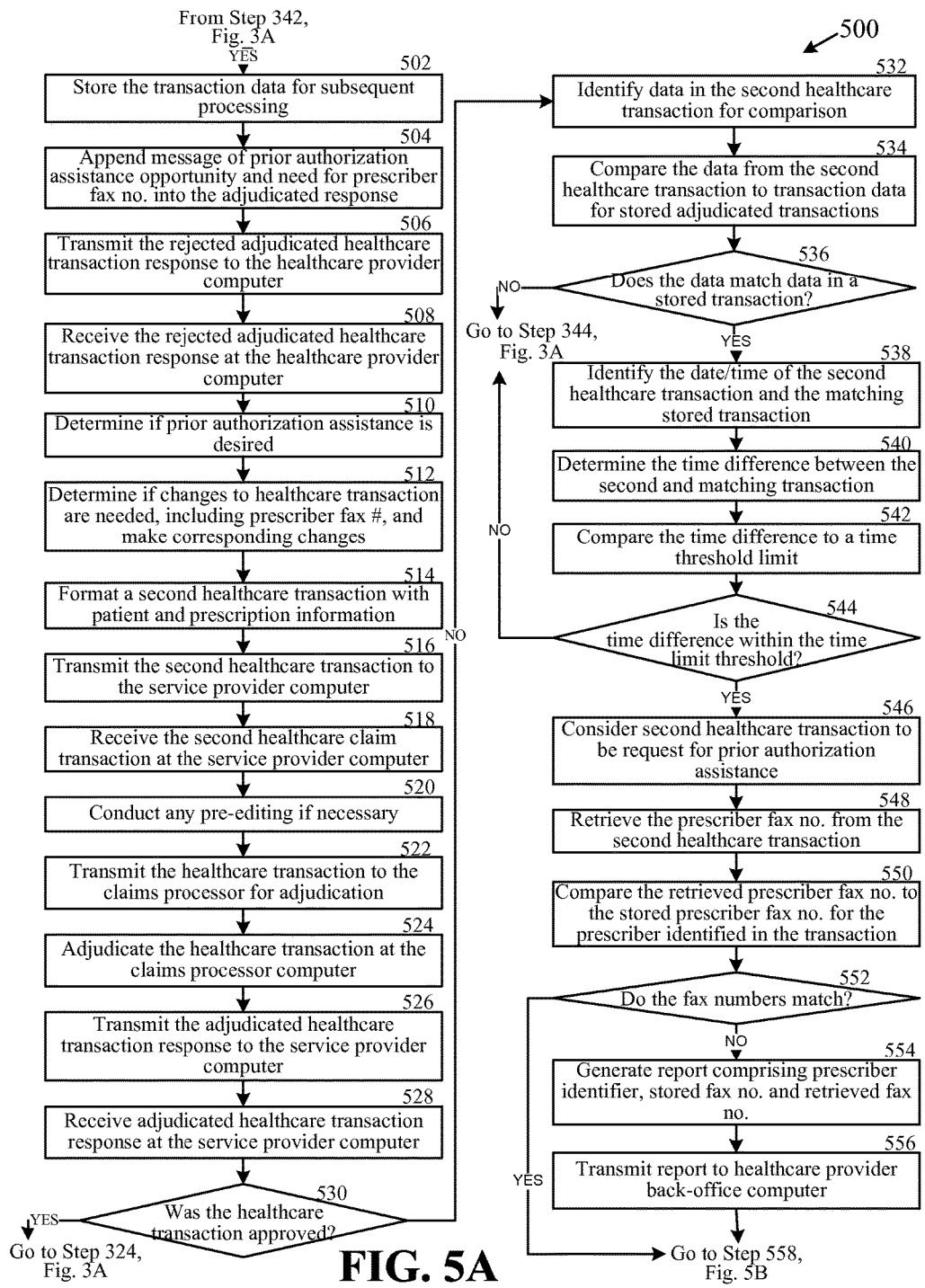
FIGS. 5A and 5B are a flow chart of an example method for determining if a healthcare provider is making a request for prior authorization assistance and verifying the contact information for a prescriber based on an evaluation of the data in the healthcare transaction and as part of the processing of a healthcare transaction, in accordance with one exemplary embodiment.
Figure 5B:
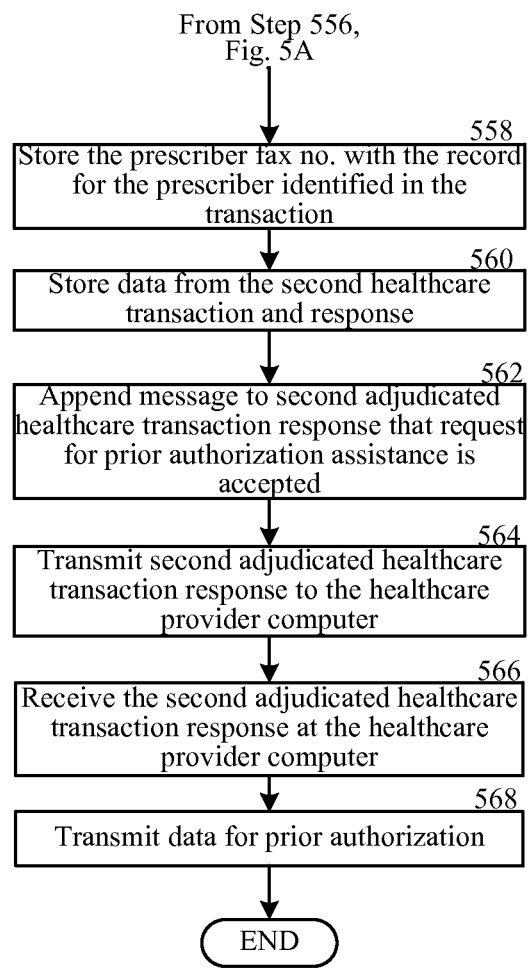

FIGS. 5A-5B are flow charts of an example method 500 for determining if a healthcare provider is making a request for prior authorization assistance and verifying contact information for a prescriber based on an evaluation of the data in the healthcare transaction and as part of the processing of the healthcare transaction, such as a predetermination of benefits transaction, a healthcare claim transaction, prescription claim or billing request, healthcare order transaction, or e-prescription transaction (e.g., electronic prescription order transaction, e-script, or e-prescription), in accordance with one exemplary embodiment. The exemplary method 500, described below, may be performed by a suitable service provider computer 106 and/or prior authorization logic module 180. Referring now to FIGS. 1, 2A, 3A, 5A, and 5B, the exemplary method 500 may begin from the YES branch of the inquiry of step 342 of FIG. 3A upon a determination that validation of the prescriber contact information (e.g., the prescriber fax number) for the prescriber that prescribed the medication/product/service in the first healthcare claim transaction 204 is needed.

In step 502, the prior authorization logic module 180 or another portion of the service provider computer 106 stores all or a portion of the first healthcare claim transaction 204 or adjudicated response 206 or all or a portion of the information from the first healthcare claim transaction 204 or adjudicated response 206 for subsequent comparison. For example the prior authorization logic module 180 or another portion of the service provider computer 106 may store all or a portion of the first healthcare claim transaction 204 or adjudicated response 206 or its data in the rejected claims database 182. The stored information can include, but is not limited to, the BIN number, PCN, any or all of the Patient Information, Prescriber ID, Healthcare Provider ID, Drug, service or product/service identifier (e.g., NDC code or RxNorm number), Fill number, prescription/service number, quantity dispensed, days' supply, and the Date of Service from the transaction 204 or 206.

In step 504, the prior authorization logic module 180 or another portion of the service provider computer 106 can modify the adjudicated first healthcare claim transaction response 206 by inserting or otherwise appending thereto a message notifying of an opportunity for receiving prior authorization assistance and a need for the pharmacy/pharmacist to submit the prescriber fax number in the following response. In one example embodiment, the message can be inserted into a text field of the adjudicated first response 206. In one example, the message can state "prior authorization assistance, sponsored by [INSERT SPONSOR NAME], available for this medication. Enter prescriber FAX # in Intermediary Authorization ID field and resubmit claim to initiate prior authorization processing."

In step 506, the service provider computer 106 transmits the adjudicated first healthcare claim transaction response 206, including the message and the basis for rejection, to the healthcare provider computer 104 via, for example, the network 110. The healthcare provider computer 104 for the pharmacy receives the rejected adjudicated first healthcare claim transaction response 206 in step 508. In step 510, the pharmacy/pharmacist and/or patient determine if they desire to receive prior authorization assistance. If they desire the assistance, pharmacy/pharmacist can generate a second healthcare claim transaction 208 without specifically making a request via the transaction or otherwise for prior authorization assistance.

The pharmacist accesses the healthcare provider computer 104, reviews the contents of the first healthcare claim transaction and determines if changes to the first healthcare claim transaction are needed, and if so, makes the corresponding changes, including adding the prescriber fax number, if necessary, to the healthcare transaction in step 412. For example, the pharmacist can make any necessary changes to the first healthcare claim transaction in preparation for resubmission of that first healthcare claim transaction as a second healthcare claim transaction. In an alternative embodiment, rather than resubmitting the first healthcare claim transaction, the pharmacist may create a new healthcare claim transaction, also referenced as a second healthcare claim transaction for submission to the service provider computer 106.

In step 514, the second healthcare claim transaction 208 is generated and/or formatted at the healthcare provider computer 104. In certain exemplary embodiments, the healthcare provider computer 104 formats the second healthcare claim transaction 208 with patient information and prescription information. For example, the information could substantially match the information in the first healthcare claim transaction 204. The second healthcare claim transaction 208 may also include any of the types of information described with reference to the first healthcare claim transaction 204 and may further include the prescriber fax number, which may be positioned within the intermediary authorization ID field of the transaction 208.

The healthcare provider computer 104 transmits the second healthcare claim transaction 208 to the service provider computer 106 in step 516. In step 518, the service provider computer 106 receives the second healthcare claim transaction 208. In step 520, the service provider computer 106 conducts any pre-editing, if necessary, on the second healthcare claim transaction 208. The pre-edits may include any of those edits described with reference to the first healthcare claim transaction 204.

The service provider computer 106 transmits the second healthcare claim transaction 208 to the claims processor computer 108 in step 522 via the network 110. The claims processor computer 108 receives and adjudicates the second healthcare claim transaction 208 in step 524 to determine if the patient has coverage, to determine to what extent the patient's coverage covers the requested medication/product/service identified in the transaction 208, and to generate a second adjudication 210 as to whether the transaction 208 is approved or rejected. In step 526, the claims processor computer 108 transmits the adjudicated second healthcare claim transaction response 210 to the service provider computer 106 via, for example, the network 110.

The service provider computer 106 receives the adjudicated second healthcare claim transaction response 210 from the claims processor computer 108 in step 528. In step 530, an inquiry is conducted to determine if the adjudicated second healthcare claim transaction response 210 indicates that the transaction was approved or paid by parsing the adjudicated second healthcare claim transaction response 210 and identifying the code in the field associated with adjudication. The prior authorization logic module 180 or another portion of the service provider computer 106 compares that identified code to a table of adjudication codes to identify a match that signifies the adjudicated response from the claims processor computer 108. If the adjudication is that the second healthcare claim transaction 208 is approved or paid, the YES branch is followed to step 324 of FIG. 3A. On the other hand, if the second adjudicated healthcare claim transaction response code indicates a denial, an inquiry is conducted to determine if the reject code identifies the rejection as being a prior authorization rejection. The service provider computer 106, for example the service provider module 156, the prior authorization logic module 180 or another portion of the service provider computer 106 can parse the adjudicated second healthcare claim transaction response 210 to identify the adjudication code and compare that code to a table, schedule, or database of adjudication codes (e.g., in the rejected claims database 182 or the data files 148) to identify a match to one or more reject codes and determine the basis for the rejection, based on that match. If the prior authorization logic module 180 identifies a match that indicates the second healthcare claim transaction 208 was denied or rejected based on a requirement for prior authorization, the NO branch is followed to step 532.

In step 532, the prior authorization logic module 180 or another portion of the service provider computer 106 identifies and/or selects data from the second healthcare claim transaction 208 or response 210 to be used for comparison in a manner substantially the same as that described in step 374 of FIG. 3B. In step 534, the prior authorization logic module 180 or another portion of the service provider computer 106 can compare the transaction comparison data from the second healthcare claim transaction 208 or response 210 to a multitude of records for previously submitted healthcare claim transactions and/or adjudicated responses stored in, for example, the rejected claims database 182 to determine if the transaction comparison data matches the data in one or more records for previously submitted healthcare claim transactions and/or adjudicated responses in a manner substantially the same as that described in step 376 of FIG. 3B.

In step 536, an inquiry is conducted to determine if the transaction comparison data for the second healthcare claim transaction 208 or adjudicated response 210 matches the data in a stored healthcare transaction or adjudicated response. In one example embodiment, the determination may be made by the prior authorization logic module 180 or another portion of the service provider computer 106 in a manner substantially the same as that described in step 378 of FIG. 3B. If a determination is made that the transaction comparison data for the second healthcare claim transaction 208 or adjudicated response 210 does not match the data in a stored healthcare transaction or response, the NO branch is followed to step 344 of FIG. 3A. On the other hand, if one or more records for stored transactions or adjudicated responses are found to be matching the transaction comparison data, the YES branch is followed to step 538.

In step 538, the prior authorization logic module 180 or another portion of the service provider computer 106 can identify the date and/or time that the second healthcare claim transaction 208 was submitted to the service provider computer 106 for processing and likewise can identify the date and/or time that the matching stored transaction or adjudicated response(s) was submitted to the service provider computer 106 for processing based on the data stored in that matching record in a manner substantially the same as that described in step 380 of FIG. 3B. The prior authorization logic module 180 or another portion of the service provider computer 106 can compare the date/time of submission of the second healthcare claim transaction 208 to the date/time of submission of the matching stored transaction to determine the time difference of submission between the second healthcare claim transaction 208 and the matching stored transaction in step 540 in a manner substantially the same as that described in step 382 of FIG. 3B.

In step 542, the prior authorization logic module 180 or another portion of the service provider computer 106 can compare the determined submission time difference to a time limit threshold to determine if the submission time difference is within (or otherwise satisfies) the time limit threshold in substantially the same manner as that discussed in step 384 of FIG. 3B. In step 544, an inquiry is conducted to determine if the submission time difference between the second healthcare claim transaction 208 and the matching transaction or adjudicated response is within the time limit threshold. In one example, the submission time difference is within the time limit threshold if it is less than or less than or equal to the time limit threshold. The determination can be made by the prior authorization logic module 180 or another portion of the service provider computer 106 and can be done by comparing the submission time difference to the time limit threshold. If the submission time difference is not within the time limit threshold, the NO branch can be followed to step 344 of FIG. 3A. If the submission time difference is within (or otherwise satisfies) the time limit threshold, the YES branch can be followed to step 546.

In step 546, based at least on the fact that the transaction comparison data for the second healthcare claim transaction 208 or adjudicated response 210 matches a stored transaction or adjudicated response and the submission time difference between the two satisfies the time limit threshold, the prior authorization logic module 180 or another portion of the service provider computer 106 can infer or otherwise consider the second healthcare claim transaction 208 to be a request for prior authorization assistance, even though nothing in the second healthcare claim transaction 208 or adjudicated response 210 specifically makes that prior authorization assistance request and the request has not been otherwise made by the pharmacy/pharmacist or patient.

In step 548, the prior authorization logic module 180 or another portion of the service provider computer 106 can retrieve the prescriber fax number from the second healthcare claim transaction 208 or adjudicated response 210. In step 550, the prior authorization logic module 180 or another portion of the service provider computer 106 compares the retrieved prescriber fax number or other contact information to a stored prescriber fax number or other contact information for the prescriber prescribing the medication/product/service in the transaction 208 to determine if there is a match. In step 552, an inquiry is conducted to determine if the fax numbers or other prescriber contact information matches. In one example embodiment, the determination is made by the prior authorization logic module 180 or another portion of the service provider computer 106. If there is a match, the YES branch is followed to step 558. Otherwise, the NO branch is followed to step 554, where a report is generated. The report can include the prescriber identifier (e.g., prescriber name, NPI code, and/or DEA number) the stored fax number or contact information for the prescriber and the retrieved fax number or contact information for the prescriber and can be generated by the prior authorization logic module 180 or another portion of the service provider computer 106. The report can be transmitted by the service provider computer 106 to a healthcare provider back office computer (e.g., a computer for the corporate headquarters of the pharmacy) via the network 110 in step 556.

In step 558, the prior authorization logic module 180 or another portion of the service provider computer 106 can store 214 the prescriber fax number with the record for the prescriber identified in the second healthcare claim transaction 208. In one example, the prescriber fax number can be retrieved from the intermediary authorization ID field of the second healthcare claim transaction 208 and can be stored with the prescriber record in the rejected claims database 182, in memory 142, or in another database.

In step 560, the prior authorization logic module 180 or another portion of the service provider computer 106 stores all or a portion of the second healthcare claim transaction 208 or adjudicated response 210 or all or a portion of the information/data from the second healthcare claim transaction 208 or adjudicated response 210 for subsequent processing and/or comparisons. For example the prior authorization logic module 180 or another portion of the service provider computer 106 may store all or a portion of the second healthcare claim transaction 208 or adjudicated response 210 or its data in the rejected claims database 182.

In step 562, the prior authorization logic module 180 or another portion of the service provider computer 106 can modify the adjudicated second healthcare claim transaction response 210 by inserting or otherwise appending thereto a message notifying the pharmacy/pharmacist or patient that the request for prior authorization assistance has been accepted and the prior authorization assistance process has been initiated. The message may further include a request to resubmit the transaction 208 within a predetermined time period, such as 48 hours. In one example embodiment, the message can be inserted into a text field of the adjudicated second response 210.

In step 564, the service provider computer 106 transmits the adjudicated second healthcare claim transaction response 210, including the message and the basis for rejection, to the healthcare provider computer 104 via, for example, the network 110. The healthcare provider computer 104 for the pharmacy receives the adjudicated second healthcare claim transaction response 210 in step 566. In step 568, the prior authorization logic module 180 or another portion of the service provider computer 106 may transmit a request for prior authorization assistance along with at least a portion of the data from the first or second healthcare claim transactions 204, 208 or adjudicated responses 206, 210 to a third-party prior authorization assistance computer via, for example, the network 110. The process then continues to the END step.

The methods described and shown in FIGS. 3A-5B may be carried out or performed in any suitable order as desired in various embodiments. Additionally, in certain exemplary embodiments, at least a portion of the operations may be carried out in parallel. Furthermore, in certain exemplary embodiments, less than or more than the operations described in FIGS. 3A-5B may be performed.

Figure 2B:
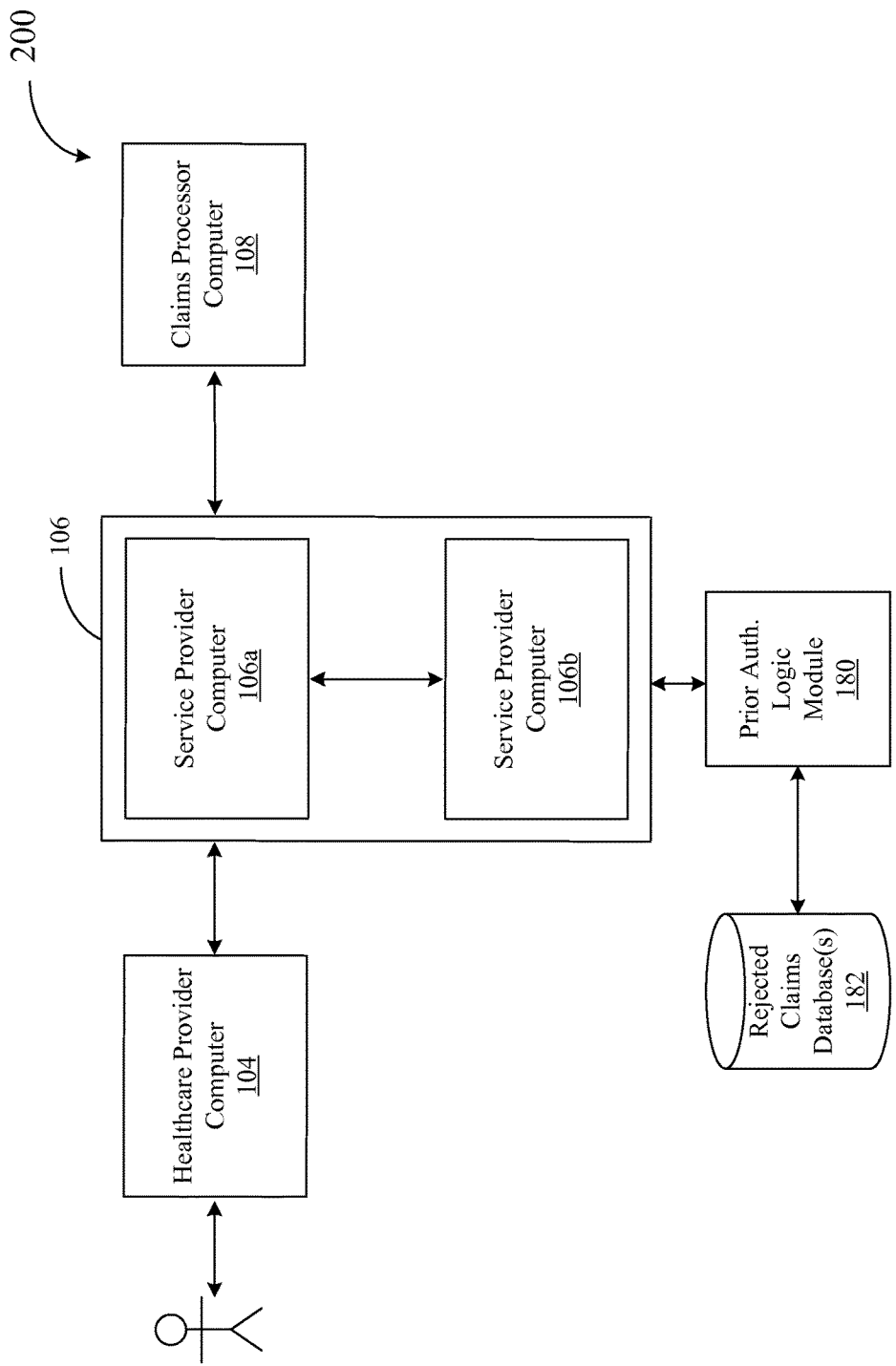
FIG. 2B is a diagram of another example data flow for determining if a healthcare provider is making a request for prior authorization assistance based on an evaluation of the data in the healthcare transaction and as part of the processing of a healthcare transaction processed through one or more service providers according to an alternative exemplary embodiment.

Likewise, while FIGS. 3A-5B have been described primarily in conjunction with FIG. 2A, it will be appreciated that variations of FIG. 2A are available. As shown by FIG. 2B, the service provider computer 106 may include two or more distinct service provider computers 106a and 106b that are in communication with each other. These distinct service provider computers 106a and 106b may be owned, operated, and/or located by the same or distinct and wholly-unrelated companies. The service provider computer 106a may be operative with the healthcare provider computer 104, while the service provider computer 106b may be operative with other healthcare provider computers and/or other third-party entity computers. However, the service provider computer 106b may have a data processing arrangement with the service provider computer 106a. Under the data processing arrangement, the service provider computer 106a may be permitted to utilize or offer services of the service provider computer 106b, including the operations and use of the prior authorization logic module 180 and the data in the rejected claims database 182 to determine if a request for prior authorization assistance may be inferred from the submission of a healthcare transaction, as discussed above. Accordingly, the services accessible by the service provider computer 106b, including the copies of transactions or transaction data in the database 182, may be available to the healthcare provider computer 104 via the service provider computers 106a and 106b.

While certain example embodiments disclosed herein describe the prior authorization logic module 180 as being separate of the service provider computer 106, in alternate embodiments, the prior authorization logic module 180 or the functions that it completes may be part of the service provider computer 106. In those embodiments where the prior authorization logic module 180 is incorporated into the service provider computer 106, and with regard to the methods described above, the elements describing transmitting or receiving between the service provider computer 106 and the prior authorization logic module 180 may be internal transmissions within the service provider computer 106 or may be omitted altogether. Further, while the exemplary embodiments described herein disclose certain steps occurring at the service provider computer 106 and/or the prior authorization logic module 180, in alternative embodiments those steps described with reference to FIGS. 1-5B may alternately be completed at a healthcare provider computer 104 (e.g., a pharmacy computer, prescriber computer, hospital computer, clinic computer, etc.), a claims processor computer 108, a prior authorization logic module 180, any combination thereof, and/or a combination of those devices along with the service provider computer 106. In those alternate embodiments, certain transmission/receiving blocks described above with reference to FIGS. 1-5B may be omitted while others may be added, as understood by one or ordinary skill in the art. The intent being that, in alternate embodiments, any of the devices/computers discussed in FIG. 1 are capable of completing all or any part of the methods described with reference to FIGS. 2A-5B.

Accordingly, example embodiments disclosed herein can provide the technical effects of creating a system and method that provides real-time or near real time way to determine whether a healthcare provider, such as a pharmacist/pharmacy, is making a request for prior authorization assistance based on an evaluation of the data in the healthcare transaction as part of or in-line with the processing of one or more types of healthcare transactions. In this regard, pharmacies and other healthcare providers may more easily make requests for prior authorization assistance or any other assistance being offered by the service provider via the service provider computer simply by resubmitting the healthcare transaction or submitting a new healthcare transaction upon receiving the notification of offer of assistance.

Although example embodiments of the disclosure have been described, one of ordinary skill in the art will recognize that numerous other modifications and alternative embodiments are within the scope of the disclosure. For example, any of the functionality and/or processing capabilities described with respect to a particular device or component may be performed by any other device or component. Furthermore, while various example implementations and architectures have been described in accordance with example embodiments of the disclosure, one of ordinary skill in the art will appreciate that numerous other modifications to the example implementations and architectures described herein are also within the scope of this disclosure.

Certain aspects of the disclosure are described above with reference to block and flow diagrams of systems, methods, apparatuses, and/or computer program products according to example embodiments. It will be understood that one or more blocks of the block diagrams and steps of the flow diagrams, and combinations of blocks in the block diagrams and steps of the flow diagrams, respectively, may be implemented by execution of computer-executable program instructions. Likewise, some blocks of the block diagrams and steps of the flow diagrams may not necessarily need to be performed in the order presented, or may not necessarily need to be performed at all, according to some embodiments. Further, additional components and/or operations beyond those depicted in blocks of the block and/or steps of the flow diagrams may be present in certain embodiments.

Accordingly, blocks of the block diagrams and steps of the flow diagrams support combinations of means for performing the specified functions, combinations of elements or steps for performing the specified functions and program instruction means for performing the specified functions. It will also be understood that each block of the block diagrams and step of the flow diagrams, and combinations of blocks in the block diagrams and steps of the flow diagrams, may be implemented by special-purpose, hardware-based computer systems that perform the specified functions, elements or steps, or combinations of special-purpose hardware and computer instructions.

Computer-executable program instructions may be loaded onto a special-purpose computer or other particular machine, a processor, or other programmable data processing apparatus to produce a particular machine, such that execution of the instructions on the computer, processor, or other programmable data processing apparatus causes one or more functions or steps specified in the flow diagrams to be performed. These computer program instructions may also be stored in a computer-readable storage medium (CRSM) that upon execution may direct a computer or other programmable data processing apparatus to function in a particular manner, such that the instructions stored in the computer-readable storage medium produce an article of manufacture including instruction means that implement one or more functions or steps specified in the flow diagrams. The computer program instructions may also be loaded onto a computer or other programmable data processing apparatus to cause a series of operational elements or steps to be performed on the computer or other programmable apparatus to produce a computer-implemented process.

Additional types of CRSM that may be present in any of the devices described herein may include, but are not limited to, programmable random access memory (PRAM), SRAM, DRAM, RAM, ROM, electrically erasable programmable read-only memory (EEPROM), flash memory or other memory technology, compact disc read-only memory (CD-ROM), digital versatile disc (DVD) or other optical storage, magnetic cassettes, magnetic tape, magnetic disk storage or other magnetic storage devices, or any other medium which can be used to store the information and which can be accessed. Combinations of any of the above are also included within the scope of CRSM. Alternatively, computer-readable communication media (CRCM) may include computer-readable instructions, program modules, or other data transmitted within a data signal, such as a carrier wave, or other transmission. However, as used herein, CRSM does not include CRCM.

Although example embodiments have been described in language specific to structural features and/or methodological acts, it is to be understood that the disclosure is not necessarily limited to the specific features or acts described. Rather, the specific features and acts are disclosed as illustrative forms of implementing the example embodiments. Conditional language, such as, among others, "can," "could," "might," or "may," unless specifically stated otherwise, or otherwise understood within the context as used, is generally intended to convey that certain example embodiments could include, while other example embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

What is claimed is:

1. A computer-implemented method, comprising:
   with reference to a routing table stored by data files of a service provider computer embodied by a switch or a router, determining a claims processor computer as a destination for a first healthcare claim transaction received from a pharmacy computer for a pharmacy and transmitting the first healthcare claim transaction to the claims processor computer for adjudication;
   receiving, by a network interface of the service provider computer associated with a service provider and comprising one or more computer processors from the claims processor computer associated with a claims processor, a first adjudicated transaction response for the first healthcare claim transaction comprising a first patient identifier for a patient; a first transaction submission time, and first transaction comparison data, wherein the first transaction comparison data comprises: a first product identifier identifying a first product or service for the patient; a first payor identifier; and a first prescription/service reference number;
   in an instance in which the first healthcare claim transaction was rejected, storing information relating to the first healthcare claim transaction in a rejected claims database in communication with the service provider computer;
   with reference to a database of adjudication codes, determining, by the service provider computer and based at least on a first reject code in the first adjudicated transaction response, that a basis for a rejection of the first healthcare claim transaction was for lack of prior authorization;

modifying, by the service provider computer and based at least in part on the rejection of the first healthcare claim transaction for lack of prior authorization, the first adjudicated transaction response to include a prior authorization offer message;

receiving, by the network interface of the service provider computer from the claims processor computer, a second adjudicated transaction response for a second healthcare claim transaction, the second healthcare claim transaction comprising a second patient identifier for the patient; a second transaction submission time, and second transaction comparison data, wherein the second transaction comparison data comprises: a second product identifier identifying the first product or service for the patient; a second payor identifier; and a second prescription/service reference number;

with reference to the database of adjudication codes, determining, by the service provider computer and based at least on a second reject code in the second adjudicated transaction response, that the second healthcare claim transaction was rejected for lack of prior authorization;

identifying the second transaction comparison data for the second healthcare claim transaction;

comparing, by the service provider computer, the second transaction comparison data to data in a plurality of records of previously processed healthcare transactions stored in the rejected claims database to identify a matching healthcare transaction record comprising matching transaction comparison data exists, wherein the matching healthcare transaction record comprises the first patient identifier; the first transaction submission time, and the first transaction comparison data from the first healthcare claim transaction;

retrieving, by the service provider computer and based at least on a positive identification of the matching healthcare transaction record, the second transaction submission time for the second healthcare claim transaction and the first transaction submission time for the matching healthcare transaction record;

calculating, by the service provider computer, a submission time difference between the second transaction submission time and the first transaction submission time;

with reference to a record containing a time threshold limit stored by the data files of the service provider computer, comparing, by the service provider computer, the submission time difference to the time limit threshold to determine if the submission time difference satisfies the time limit threshold;

determining, by the service provider computer and based at least in part on the positive determination that the submission time difference satisfies the time limit threshold, that the second healthcare claim transaction is a request for prior authorization assistance; and modifying, by the service provider computer and based at least in part on the rejection of the second healthcare claim transaction for lack of prior authorization, a second adjudicated transaction response to include a prior authorization assistance request acceptance message.

2. The computer-implemented method of claim 1, further comprising:

wherein modifying the first adjudicated transaction response comprises appending, by the service provider computer, the prior authorization offer message to the first adjudicated transaction response, and wherein the method further comprises:

transmitting, by the service provider computer to the pharmacy computer for the pharmacy, the first adjudicated transaction response and the prior authorization offer message.

3. The computer-implemented method of claim 1, further comprising:

receiving, by the service provider computer from the pharmacy computer for the pharmacy, the first healthcare claim transaction;

receiving, by the service provider computer from the pharmacy computer, the second healthcare claim transaction; and transmitting, by the service provider computer to the claims processor computer, the second healthcare claim transaction for adjudication.

4. The computer-implemented method of claim 1 wherein modifying the second adjudicated transaction response comprises appending, by the service provider computer, the prior authorization assistance request acceptance message to the second adjudicated transaction response; and transmitting, by the service provider computer to the pharmacy computer, the second adjudicated transaction response and the prior authorization assistance request acceptance message;

generating, by the service provider computer and based at least in part on the request for prior authorization assistance and one or more of the first and second healthcare claim transactions, a prior authorization assistance request; and transmitting, by the service provider computer, the prior authorization assistance request to a prior authorization assistance computer.

5. A computer-implemented method, comprising:

with reference to a routing table stored by data files of a service provider computer embodied by a switch or a router, determining a claims processor computer as a destination for a first healthcare claim transaction received from a pharmacy computer for a pharmacy and transmitting the first healthcare claim transaction to the claims processor computer for adjudication;

receiving, by a network interface of the service provider computer associated with a service provider from the claims processor computer, a first adjudicated transaction response for the first healthcare claim transaction comprising a first patient identifier for a patient, a first transaction submission time, and first transaction comparison data;

in an instance in which the first healthcare claim transaction was rejected, storing information relating to the first healthcare claim transaction in a rejected claims database in communication with the service provider computer;

modifying, by the service provider computer and based at least in part on the first healthcare claim transaction being rejected for lack of prior authorization, the first adjudicated transaction response to include a prior authorization offer message;

transmitting, by the network interface of the service provider computer to the pharmacy computer for the pharmacy, the first adjudicated transaction response and the prior authorization offer message;

receiving, by the network interface of the service provider computer from the claims processor computer, a second adjudicated transaction response for a second healthcare claim transaction, the second healthcare claim transaction comprising a second patient identifier for the patient; a second transaction submission time, and second transaction comparison data;

comparing, by the service provider computer, the second transaction comparison data to data in a plurality of records of previously processed healthcare transactions stored in the rejected claims database to identify a matching healthcare transaction record comprising matching transaction comparison data exists, wherein the matching healthcare transaction record comprises the first transaction submission time and the first transaction comparison data;

retrieving, by the service provider computer, the second transaction submission time and the first transaction submission time;

calculating, by the service provider computer, a submission time difference between the second transaction submission time and the first transaction submission time;

with reference to a record containing a time threshold limit stored by the data files of the service provider computer, comparing, by the service provider computer, the submission time difference to the time limit threshold to determine if the submission time difference satisfies the time limit threshold;

determining, by the service provider computer and based at least in part on the positive determination that the submission time difference satisfies the time limit threshold, that the second healthcare claim transaction is a request for the prior authorization service; and modifying, by the service provider computer and based at least in part on the second healthcare claim transaction being rejected for lack of prior authorization, a second adjudicated transaction response to include a prior authorization assistance request acceptance message.

6. The computer-implemented method of claim 5, wherein the method further comprises:
  determining, by the service provider computer and based at least on a reject code in the second adjudicated transaction response, that the second healthcare claim transaction was rejected for lack of prior authorization;
  wherein comparing the second transaction comparison data to data in the plurality of records of previously processed healthcare transactions is completed based at least in part on the determination that the second healthcare claim transaction was rejected for lack of prior authorization.

7. The computer-implemented method of claim 5, wherein the second transaction comparison data comprises: a product identifier identifying a product or service for the patient; a payor identifier; a prescription/service reference number; a banking identification number, a processor control number, a fill number, a quantity dispensed, and a days' supply.

8. The computer-implemented method of claim 5, wherein the method further comprises:
  transmitting, by the service provider computer to the pharmacy computer, the prior authorization assistance request acceptance message;
  generating, by the service provider computer and based at least in part on the request for prior authorization assistance and one or more of the first and second healthcare claim transactions, a prior authorization assistance request; and
  transmitting, by the service provider computer, the prior authorization assistance request to a prior authorization assistance computer.

9. The computer-implemented method of claim 5, further comprising:
  receiving, by the service provider computer from the pharmacy computer, the first healthcare claim transaction, wherein the first healthcare claim transaction further comprises a prescriber identifier;
  transmitting, by the service provider computer to the claims processor computer, the first healthcare claim transaction for adjudication;
  determining, by the service provider computer and based at least in part on the prescriber identifier, if a stored record for the prescriber identified by the prescriber identifier comprises a prescriber facsimile number;
  generating, by the service provider computer and based at least in part on the determination that the stored record does not comprise the prescriber facsimile number, a request for the prescriber facsimile number; and
  appending, by the service provider computer, the request to the first adjudicated transaction response that is transmitted to the pharmacy computer.

10. The computer-implemented method of claim 9, wherein the second healthcare claim transaction further comprises the prescriber identifier and prescriber facsimile number and wherein the method further comprises:
  retrieving, by the service provider computer, the prescriber facsimile number; and
  electronically storing, by the service provider computer, the prescriber facsimile number in the stored record for the prescriber.

11. The computer-implemented method of claim 5, further comprising:
  receiving, by the service provider computer from the pharmacy computer, the first healthcare claim transaction, wherein the first healthcare claim transaction further comprises a prescriber identifier;
  determining, by the service provider computer and based at least in part on the prescriber identifier, if a stored record for the prescriber identified by the prescriber identifier comprises a prescriber facsimile number;
  determining, by the service provider computer and based at least in part on the determination that the stored record does comprise the prescriber facsimile number, that the prescriber facsimile number needs to be validated;
  generating, by the service provider computer and based at least in part on the determination that the stored prescriber facsimile number needs to be validated, a request for the prescriber facsimile number;
  appending, by the service provider computer, the request to the first adjudicated transaction response that is transmitted to the pharmacy computer;
  retrieving, by the service provider computer, the requested prescriber facsimile number from the second healthcare claim transaction;
  comparing, by the service provider computer, the requested prescriber facsimile number to the stored facsimile number to determine if the requested facsimile number matches the stored facsimile number; and electronically storing, by the service provider computer, the requested prescriber facsimile number in the stored record for the prescriber based at least on a positive determination that the requested prescriber facsimile number does not match the stored prescriber facsimile number.

12. The computer-implemented method of claim 5, wherein the method further comprises:
identifying, by the service provider computer, a first reject code in the first adjudicated transaction response; and
determining, by the service provider computer and based at least on the first reject code, that a basis for a rejection of the first healthcare claim transaction was for lack of prior authorization.

13. A system embodied by a switch or a router, the system comprising;
at least one memory operable to store computer-executable instructions and data files including a routing table and a record containing a time threshold limit;
a network interface; and
at least one processor configured to access the at least one memory and execute the computer-executable instructions to:
with reference to the routing table, determine a claims processor computer as a destination for a first healthcare claim transaction received from a pharmacy computer for a pharmacy and transmit the first healthcare claim transaction to the claims processor computer for adjudication;
receive, via the network interface from the claims processor computer, a first adjudicated transaction response for the first healthcare claim transaction comprising a first patient identifier for a patient; a first transaction submission time, and first transaction comparison data;
in an instance in which the first healthcare claim transaction was rejected, store information relating to the first healthcare claim transaction in a rejected claims database in communication with the system;
modify, based at least in part on the first healthcare claim transaction being rejected for lack of prior authorization, the first adjudicated transaction response to include a prior authorization offer message;
direct communication, via the network interface to the pharmacy computer for the pharmacy, of the first adjudicated transaction response and the prior authorization offer message;
receive, via the network interface from the claims processor computer, a second adjudicated transaction response for a second healthcare claim transaction, the second healthcare claim transaction comprising a second patient identifier for the patient; a second transaction submission time, and second transaction comparison data;
compare the second transaction comparison data to data in a plurality of records of previously processed healthcare transactions stored in the rejected claims database to identify a matching healthcare transaction record comprising matching transaction comparison data exists, wherein the matching healthcare transaction record comprises the first transaction submission time and the first transaction comparison data;
receive the second transaction submission time and the first transaction submission time;
calculate a submission time difference between the second transaction submission time and the first transaction submission time;
with reference to the record containing the time threshold limit stored by the data files, compare the submission time difference to the time limit threshold to determine if the submission time difference satisfies the time limit threshold;
determine, based at least in part on the positive determination that the submission time difference satisfies the time limit threshold, that the second healthcare claim transaction is a request for the prior authorization service; and
modify, based at least in part on the second healthcare claim transaction being rejected for lack of prior authorization, a second adjudicated transaction response to include a prior authorization assistance request acceptance message.

14. The system of claim 13, wherein the processor is further configured to access the at least one memory and execute the computer-executable instructions to:
determine, based at least on a reject code in the second adjudicated transaction response, that the second healthcare claim transaction was rejected for lack of prior authorization;
wherein comparing the second transaction comparison data to data in the plurality of records of previously processed healthcare transactions is completed based at least in part on the determination that the second healthcare claim transaction was rejected for lack of prior authorization.

15. The system of claim 13, wherein the second transaction comparison data comprises: a product identifier identifying a product or service for the patient; a payor identifier; a prescription/service reference number; a banking identification number, a processor control number, a fill number, a quantity dispensed, and a days' supply.

16. The system of claim 13, wherein the processor is further configured to access the at least one memory and execute the computer-executable instructions to:
direct communication, to the pharmacy computer, of the prior authorization assistance request acceptance message;
generate, based at least in part on the request for prior authorization assistance and one or more of the first and second healthcare claim transactions, a prior authorization assistance request; and
direct communication of the prior authorization assistance request to a prior authorization assistance computer.

17. The system of claim 13, wherein the processor is further configured to access the at least one memory and execute the computer-executable instructions to:
receive, from the pharmacy computer, the first healthcare claim transaction, wherein the first healthcare claim transaction further comprises a prescriber identifier;
determine, based at least in part on the prescriber identifier, if a stored record for the prescriber identified by the prescriber identifier comprises a prescriber facsimile number;
generate, based at least in part on the determination that the stored record does not comprise the prescriber facsimile number, a request for the prescriber facsimile number; and
append the request to the first adjudicated transaction response that is transmitted to the pharmacy computer.

18. The system of claim 17, wherein the second healthcare claim transaction further comprises the prescriber identifier and prescriber facsimile number and wherein the processor is further configured to access the at least one memory and execute the computer-executable instructions to:
- receive the prescriber facsimile number; and
- electronically store the prescriber facsimile number in the stored record for the prescriber.

19. The system of claim 13, wherein the processor is further configured to access the at least one memory and execute the computer-executable instructions to:
- receive, from the pharmacy computer, the first healthcare claim transaction, wherein the first healthcare claim transaction further comprises a prescriber identifier;
- determine, based at least in part on the prescriber identifier, if a stored record for the prescriber identified by the prescriber identifier comprises a prescriber facsimile number;
- determine, based at least in part on the determination that the stored record does comprise the prescriber facsimile number, that the prescriber facsimile number needs to be validated;
- generate, based at least in part on the determination that the stored prescriber facsimile number needs to be validated, a request for the prescriber facsimile number;
- append the request to the first adjudicated transaction response that is transmitted to the pharmacy computer;
- retrieve the requested prescriber facsimile number from the second healthcare claim transaction;
- compare the requested prescriber facsimile number to the stored facsimile number to determine if the requested facsimile number matches the stored facsimile number; and
- electronically store the requested prescriber facsimile number in the stored record for the prescriber based at least on a positive determination that the requested prescriber facsimile number does not match the stored prescriber facsimile number.

20. The system of claim 13, wherein the processor is further configured to access the at least one memory and execute the computer-executable instructions to:
- identify a first reject code in the first adjudicated transaction response; and
- determine, based at least on the first reject code, that a basis for a rejection of the first healthcare claim transaction was for lack of prior authorization.

\* \* \* \* \*